(12) United States Patent
Matsui et al.

(10) Patent No.: US 7,503,965 B2
(45) Date of Patent: Mar. 17, 2009

(54) AZO COMPOUND, INK COMPOSITION, AND COLORED OBJECT

(75) Inventors: Takahiko Matsui, Kita-ku (JP); Hiroaki Ohno, Kita-ku (JP); Takashi Yoneda, Kita-ku (JP); Yasuo Shirasaki, Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 381 days.

(21) Appl. No.: 11/547,302

(22) PCT Filed: Apr. 6, 2005

(86) PCT No.: PCT/JP2005/006780

§ 371 (c)(1),
(2), (4) Date: Oct. 4, 2006

(87) PCT Pub. No.: WO2005/097912

PCT Pub. Date: Oct. 20, 2005

(65) Prior Publication Data

US 2008/0292792 A1    Nov. 27, 2008

(30) Foreign Application Priority Data

Apr. 9, 2004    (JP)    ............... 2004-115073

(51) Int. Cl.
 C09D 11/00    (2006.01)
 C09D 11/02    (2006.01)
 C09B 35/50    (2006.01)
 B41J 2/01    (2006.01)
(52) U.S. Cl. .............. 106/31.5; 534/754; 347/100
(58) Field of Classification Search .............. 106/31.5; 534/754; 347/100
 See application file for complete search history.

(56) References Cited

U.S. PATENT DOCUMENTS 4,395,288 A * 7/1983 Eida et al. ............. 106/31.51
4,426,226 A * 1/1984 Ohta et al. ............. 106/31.52
7,041,161 B2 * 5/2006 Mistry et al. ............. 106/31.5
7,052,538 B2 * 5/2006 Mistry et al. ............. 106/31.5
7,326,288 B2 * 2/2008 Matsui et al. ............. 106/31.52
7,462,228 B2 * 12/2008 Ohno et al. ............. 534/806
7,465,346 B2 * 12/2008 Fukumoto et al. ........ 106/31.5
2003/0187236 A1   10/2003 Sawatari
2006/0144288 A1   7/2006 Ohno
2007/0109376 A1 * 5/2007 Tojo et al. ............. 106/31.5
2007/0139499 A1 * 6/2007 Yabuki et al. ............. 106/31.5
2008/0193660 A1 * 8/2008 Matsui et al. ............. 427/421.1

FOREIGN PATENT DOCUMENTS

| JP | 62-109872 | 5/1987 |
| JP | 2003-183545 | 7/2003 |
| JP | 2003-201412 | 7/2003 |
| JP | 2004-285351 A1 | 10/2004 |
| JP | 2006/076908 * | 3/2006 |

OTHER PUBLICATIONS

English translation of JP2006/076908, Mar. 2006.*
The International Search Report dated Jul. 5, 2005.

* cited by examiner

*Primary Examiner*—Helene Klemanski
(74) *Attorney, Agent, or Firm*—Nields, Lemack & Frame, LLC

(57) ABSTRACT

A novel azo compound represented by the following Formula (1) wherein A represents the following Formula (2) and is located preferably in a position meta or para to the azo group; $R^1$ and $R^2$ each independently represents hydrogen, carboxy, sulfo, nitro, $C_{1-4}$ alkoxy, etc.; $R^3$ and $R^4$ each independently represents hydrogen, halogeno, cyano, carboxy, sulfo, nitro, $C_{1-4}$ alkyl, hydroxy, or $C_{1-4}$ alkoxy; and n is 0 or 1. [In the Formula (2), $R^5$ represents cyano, carboxy, $C_{1-4}$ alky, $C_{1-4}$ alkoxycarbonyl, or phenyl; and $R^6$, $R^7$, and $R^8$ each independently represents hydrogen, halogeno, cyano, carboxy, sulfo, nitro, $C_{1-4}$ alkyl, $C_{1-4}$ alkoxy, or acylamino.] The compound is useful as a black dye, especially one for ink compositions for, e.g., inkjet prints. Also provided are: an ink composition which contains the compound and has excellent storage stability; and a print obtained through recording with the ink. The print is excellent in light resistance, ozone resistance, fastness to moisture, etc.

25 Claims, No Drawings

AZO COMPOUND, INK COMPOSITION, AND COLORED OBJECT

TECHNICAL FIELD

The present invention relates to a novel azo compound or a salt thereof, an ink composition comprising them, and colored object thereby.

BACKGROUND OF THE INVENTION

A method for recording by means of an ink-jet printer, a typical method among various color recording methods, recorded by generating ink droplets and depositing them onto various record-receiving materials (such as paper, film and cloth). This method has been rapidly prevailing lately and is expected to grow remarkably in the future because of such features as less noise generation due to no contact of a recording head with a record-receiving material and easiness in downsizing and speedup. Conventionally, as an ink for a fountain pen or a felt pen and an ink for ink-jet recording, a water-based ink dissolving a water-soluble dye in an aqueous medium has been used, and in these water-soluble inks, a water-soluble organic solvent is generally added to prevent ink from clogging at a pen tip or an ink-jet nozzle. These conventional inks are required to provide a recorded image of sufficient density, not to clog at a pen tip or an ink-jet nozzle, to dry quickly on a record-receiving material, to bleed less, to have good storage stability and, in particular, to have high solubility in water and a water-soluble organic solvent to be added to the inks. Moreover, an image formed is required to have image fastness such as water fastness, light fastness, ozone gas fastness and moisture fastness.

Ozone gas fastness, called ozone fastness or gas fastness in short, means durability against phenomenon that oxidizing ozone gas in the air reacts with a dye on a recording paper to incur discoloration or fading of a printed image. Although oxidizing gas having this kind of action includes NOx and SOx besides ozone gas, ozone gas is said to be a causative main substance to promote the phenomenon of discoloration or fading of an ink-jet recorded image more strongly, among these oxidizing gases. In particular, for an ink-receiving layer provided at the surface of a photographic paper special for ink-jet image, so as to dry the ink faster and decrease bleed in high quality image, porous materials of inorganic white pigments and the like are often used. Discoloration or fading in color caused by ozone gas occurs noticeably on such recording papers.

It is considered that this is because ozone contained in the air contacts with silica, alumina and the like of porous white inorganic materials contained in a recording paper and generates radicals having strong oxidizing properties, which act on coloring matter to incur discoloration or fading. As the phenomenon of discoloration or fading caused by oxidizing gas are characteristics of ink-jet images, improvement of ozone gas fastness is one of the most important problems in this field.

To extend application field of a printing method using ink in the future, an ink composition to be used for ink-jet recording and a colored object thereby are strongly required to exhibit further improved water fastness, light fastness, moisture fastness and ozone gas fastness.

Among inks with various hues prepared from various dyes, a black ink is an important one used for both of mono color and full color images. So far many dye stuffs for black inks have been proposed, however, a product sufficiently satisfying market needs has not yet been provided. Many of coloring matters proposed are disazo ones, which have problems that they have too light hues (black tinged with a red), poor color rendering (a property that hue is changed by a light source), less water and/or moisture fastness, insufficient ozone gas fastness and the like. Moreover, similarly, in the case of metal-containing azo coloring matter often proposed, they have problems such that considerations for safety to human bodies and environment are not enough because they contain metal ions, and ozone gas fastness is not sufficient. Polyazo coloring matter whose conjugated bonds were increased to deepen hues, which has been studied and developed, leave problems such as low hues density, poor solubility in water, poor storage stability in aqueous solution and ink, and insufficient ozone gas fastness.

As a coloring matter compound for black ink used for ink-jet having improved ozone gas fastness which has been the most important problems recently, for example, those described in Patent Literature 1 can be cited. However, the ozone gas fastness of those compounds doesn't satisfy market needs sufficiently. Furthermore, as structurally analogous compounds to coloring matter compounds for black inks according to the present invention, those described in Patent Literatures 2 or 3 can be cited, however, they don't satisfy market needs, particularly concerning ozone gas fastness.

Patent Literature 1: JP Laid-Open No. 183545/2003
Patent Literature 2: JP Laid-Open No. 109872/1987
Patent Literature 3: JP Laid-Open No. 201412/2003

DISCLOSURE OF THE INVENTION

Problems to be Solved by the Invention

An object according to the present invention is to provide a coloring matter for a black ink and an ink composition thereof that has high solubility in medium whose main component is water, stability in long-term storage of high concentrated aqueous dye solution and ink, high density of a printed image, fastness of a printed image, that gives a black recorded image with especially excellent ozone gas fastness, and that is also easy to synthesize and inexpensive.

Means of Solving the Problems

The inventors intensively studied a way to solve the above problems, and thus have completed the present invention. That is, the present invention relates to:

(1) An azo compound represented by Formula (1) as shown below or a salt thereof;

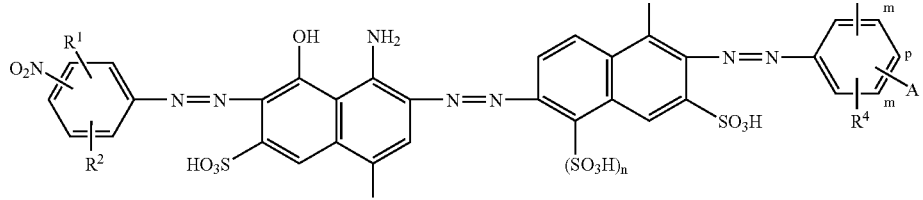

[Formula 1]

(1)

(Wherein, A represents the following Formula (2): A's substitution position is the meta-position or the para-position to an azo group: each of $R^1$ and $R^2$ independently represents a hydrogen atom; a halogen atom; a cyano group; a carboxyl group; a sulfo group; a sulfamoyl group; an N-alkylaminosulfonyl group; an N-phenylaminosulfonyl group; a phospho group; a nitro group; an acyl group; a ureide group; a (C1 to C4) alkyl group which may be substituted with a hydroxyl group or a (C1 to C4) alkoxy group; a (C1 to C4) alkoxy group which may be substituted with a hydroxyl group, a (C1 to C4) alkoxy group, a sulfo group or a carboxyl group; or an acylamino group which can be substituted with a (C1 to C4) alkoxy group, a sulfo group or a carboxyl group: each of $R^3$ and $R^4$ independently represents a hydrogen atom; a halogen atom; a cyano group; a carboxyl group; a sulfo group; a nitro group; a (C1 to C4) alkyl group; a hydroxyl group; or a (C1 to C4) alkoxy group which may be substituted with a (C1 to C4) alkoxy group or a sulfo group: and n represents 0 or 1.)

[Formula 2]

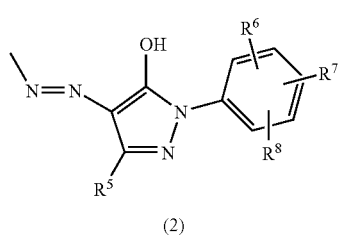

(2)

(Wherein, $R^5$ represents a cyano group; a carboxyl group; a (C1 to C4) alkyl group; a (C1 to C4) alkoxycarbonyl group; or a phenyl group: and each of $R^6$, $R^7$ and $R^8$ independently represents a hydrogen atom; a halogen atom; a cyano group; a carboxyl group; a sulfo group; a nitro group; a (C1 to C4) alkyl group; a (C1 to C4) alkoxy group which may be substituted with a hydroxyl group, a (C1 to C4) alkoxy group or a sulfo group; or an acylamino group which may be substituted with a hydroxyl group, a (C1 to C4) alkoxy group or a sulfo group.)

(2) The azo compound or the salt thereof according to the above aspect (1), wherein in Formula (1), $R^1$ is a carboxyl group, a sulfo group or a (C1 to C4) alkoxy group, and $R^2$ is a hydrogen atom or a sulfo group;

(3) The azo compound or the salt thereof according to the above aspect (1) or (2), wherein in Formula (1), relating to positions of $NO_2$, $R^1$ and $R^2$, when $NO_2$ is at the para-position and $R^1$ is at the ortho-position, $R^2$ is at the meta-position, or when $NO_2$ is at the meta-position $R^1$ is a sulfo group at the para-position and $R^2$ is a hydrogen atom;

(4) The azo compound or the salt thereof according to the above aspects (1) to (3), wherein in Formula (1), n is 1, $R^3$ is a sulfo group or a carboxyl group, and $R^4$ is a hydrogen atom, a (C1 to C4) alkyl group, $NO_2$, a sulfo group, a (C1 to C4) alkoxy group, a halogen atom or a carboxyl group;

(5) The azo compound or the salt thereof according to the above aspect (4), wherein in Formula (1), n is 1, $R^3$ is a sulfo group, and $R^4$ is a hydrogen atom, a sulfo group, a chlorine atom, or a carboxyl group;

(6) The azo compound or the salt thereof according to the above aspects (1) to (5), wherein in Formula (2), $R^5$ is a carboxyl group, $R^6$ is a hydrogen atom, a halogen atom or a (C1 to C4) alkyl group, $R^7$ is a carboxyl group or a sulfo group, and $R^8$ is a hydrogen atom, a halogen atom, a carboxyl group or a sulfo group;

(7) The azo compound or the salt thereof according to the above aspects (1) to (6), wherein in Formula (2), $R^5$ is a carboxyl group, and a phenyl group substituted with $R^6$, $R^7$ and $R^8$ is p-sulfophenyl, 2,5-disulfophenyl or 3,5-dicarboxyphenyl;

(8) The azo compound or the salt thereof according to the above aspects (1) to (7), wherein in Formula (1), $R^2$ is a hydrogen atom and $R^1$ is a carboxyl group or a sulfo group;

(9) The azo compound or the salt thereof according to the above aspects (1) to (8), wherein in Formula (1), $R^1$ is a carboxyl group, a sulfo group or a (C1 to C4) alkoxy group: $R^2$ is a hydrogen atom or a sulfo group: relating to positions of $NO_2$, $R^1$ and $R^2$, $NO_2$ is at the para-position, $R^1$ is at the ortho-position and $R^2$ is at the meta-position, or when $NO_2$ is at the ortho-position, $R^1$ is a sulfo group at the para-position and $R^2$ is a hydrogen atom, n is 1, $R^3$ is a sulfo group, and $R^4$ is a hydrogen atom, a sulfo group, a chlorine atom or a carboxyl group, and in Formula (2), $R^5$ is a carboxyl group, and a phenyl group substituted with $R^6$, $R^7$ and $R^8$ is p-sulfophenyl group, 2,5-disulfophenyl group or 3,5-dicarboxyphenyl group;

(10) An azo compound represented by Formula (3) as shown below or a salt thereof according to the above aspect (1);

[Formula 3]

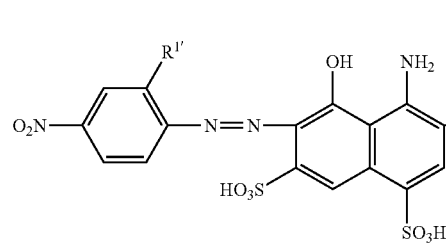

(3)

(Wherein, B represents Formula (4): B's substitution position is the meta-position or the para-position to an azo group: $R^{1'}$ represents a sulfo group or a carboxyl group: and $R^3$ and $R^4$ have the same meanings as in Formula (1) of the above aspect (1).)

[Formula 4]

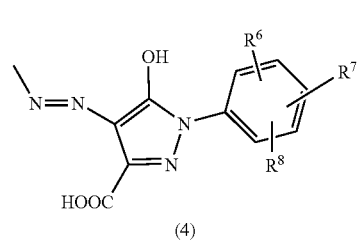

(4)

(Wherein, $R^6$, $R^7$ and $R^8$ have the same meanings as in Formula (2) in (1).)

(11) The azo compound or the salt thereof according to the aspect (10), wherein $R^3$ is a hydrogen atom, a halogen atom, a carboxyl group, a sulfo group, a nitro group or a (C1 to C4) alkyl group: $R^4$ is a hydrogen atom, a sulfo group or a nitro group: $R^6$ is a hydrogen atom, a halogen atom or a (C1 to C4) alkyl group: $R^7$ is a sulfo group or a carboxyl group: and $R^8$ is a hydrogen atom, a halogen atom, a carboxyl group or a sulfo group;

(12) An azo compound represented by Formula (5) as shown below or a salt thereof according to the above aspect (1);

tion is the meta-position or the para-position to an azo group: each of $R^1$ and $R^2$ is independently a hydrogen atom; a carboxyl group; a sulfo group; or a (C1 to C4) alkoxy group which may be substituted with a sulfo group: each of $R^3$ and $R^4$ is independently a hydrogen atom; a halogen atom; a carboxyl group; a sulfo group; a nitro group; a (C1 to C4) alkyl group; or a (C1 to C4) alkoxy group: and n is 0 or 1, and in Formula (2), $R^5$ is a cyano group; a carboxyl group; a (C1 to C4) alkyl group; or a phenyl group: and each of $R^6$, $R^7$ and $R^8$ is independently a hydrogen atom, a halogen atom; a carboxyl group; a sulfo group; or a (C1 to C4) alkyl group;

[Formula 5]

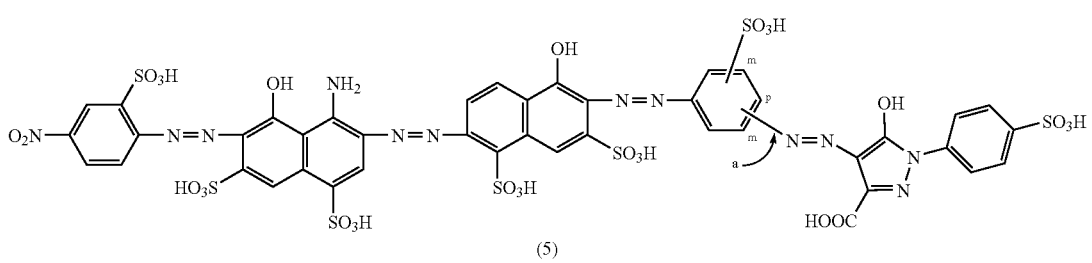

(5)

(Wherein, bond a's bonding position is the meta-position or the para-position to an azo group.)

(13) The salt of the azo compound according to any one of the above aspects (1) to (12), wherein the salt is a lithium salt, a sodium salt, a potassium salt, an ammonium salt, or an ammonium salt represented by the general Formula (6);

[Formula 6]

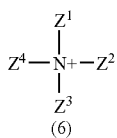

(6)

(Wherein, each of $Z^1$, $Z^2$, $Z^3$ and $Z^4$ independently represents a hydrogen atom, an alkyl group, a hydroxyalkyl group or a hydroxyalkoxyalkyl group.)

(14) An ink composition characterized by comprising at least one kind of an azo compound or a salt thereof according to any one of the above aspects (1) to (13);

(15) A recording method of ink-jet printing by applying the ink composition according to the above aspect (14) to a record-receiving material by an ink-jet printer;

(16) The recording method of ink-jet printing according to the above aspect (15), wherein a record-receiving material for a method of ink-jet printing is a sheet for transmitting information;

(17) The recording method of ink-jet printing characterized by that a sheet for transmitting information described in the above aspect (16) comprises a white inorganic matter;

(18) An ink-jet printer loaded with an ink container filled with the ink composition according to the above aspect (14);

(19) A colored object colored by the azo compound or the salt thereof according to any one of the above aspects (1) to (13);

(20) The azo compound or the salt thereof according to the aspect (1), wherein in Formula (1), A's substitution posi-

(21) The compound according to the above aspects (1) to (13), wherein a substitution position of substituent A in Formula (1), substituent B in Formula (3) or a corresponding group thereto is the para-position to an azo group;

(22) The azo compound or the salt thereof according to the above aspect (10), wherein $R^{1'}$ is a sulfo group: B's substitution position is the para-position to an azo group: $R^3$ is a sulfo group substituted at the meta-position: $R^4$ is a halogen atom or a carboxyl group substituted at the meta-position which is different from $R^3$: $R^6$ and $R^8$ are hydrogen atoms: and $R^7$ is a sulfo group;

(23) The azo compound or the salt thereof according to the above aspect (11), wherein $R^7$ is a sulfo group;

(24) An ink composition characterized by comprising at least one kind of an azo compound or a salt thereof according to any one of the above aspects (20), (22) and (23);

(25) A recording method of ink-jet printing by applying the ink composition according to the above aspect (24) to a record-receiving material by an ink-jet printer.

Effect of the Invention

An azo compound of the present invention has excellent water-solubility, therefore a filtration property with a membrane filter during production steps of ink composition is favorable, and it exhibits excellent stability in storage of a recording solution and jet stability. Furthermore, an ink composition according to the present invention comprising the azo compound does not exhibit crystal deposition, change in physical property, or color change after storage for a long period of time, and exhibits favorable storage stability. And an ink composition comprising the azo compound of the present invention is used for ink-jet recording, and for writing tools, and when a recording image is made on a plain paper and a professional paper for ink-jet, printing density of a recorded image is high and fastness of various properties, in particular, ozone gas fastness is excellent. By using it together with a magenta, a cyan, and a yellow dye, full-colored ink-jet recording with excellence in fastness of various properties is possible. Thus an ink composition according to the present invention is extremely useful as a black ink for ink-jet recording.

BEST MODE FOR CARRYING OUT THE INVENTION

The present invention will be described in detail hereinafter.

In the present invention, when "alkyl" or "alkoxy" is simply mentioned, the number of carbons thereof is not particularly limited, but usually, about 1 to 10 of carbons thereof is preferable, more preferably about 1 to 4 of carbons thereof. In addition, when "acyl" is mentioned, any of the aliphatic or the aromatic can be, but for the aliphatic, about 1 to 10 of carbons thereof is preferable, more preferably about 1 to 6 of carbons thereof, and in general about 1 to 4 of carbons thereof is preferable. For the aromatic, the carbon number of an aromatic ring thereof is preferably about 6 to 10. Additionally, "sulfo" means a sulfonic acid group.

In $R^1$ and $R^2$ in General Formula (1), examples of an N-alkylaminosulfonyl group include a mono- or di-(C1 to C4) alkylaminosulfonyl group, for example, N-methylaminosulfonyl, N-ethylaminosulfonyl, N-(n-butyl)aminosulfonyl, N,N-dimethylaminosulfonyl, N,N-di(n-propyl)aminosulfonyl and the like.

In $R^1$ and $R^2$ in General Formula (1), examples of an acyl group include, for example, acetyl, propionyl, butylyl, isobutylyl, benzoyl, naphthoyl, and the like.

In $R^1$ and $R^2$ in General Formula (1), examples of an (C1 to C4) alkyl group which may be substituted with a hydroxy group or a (C1 to C4) alkoxy group include, for example, methyl, ethyl, n-propyl, isopropyl, n-butyl, isobutyl, sec-butyl, tert-butyl, 2-hydroxyethyl, 2-hydroxypropyl, 3-hydroxypropyl, methoxyethyl, 2-ethoxyethyl, n-propoxyethyl, isopropoxyethyl, n-butoxyethyl, methoxypropyl, ethoxypropyl, n-propoxypropyl, isopropoxybutyl, n-propoxybutyl, and the like.

In $R^1$ to $R^4$ and $R^6$ to $R^8$ in General Formula (1) and General Formula (2), examples of a (C1 to C4) alkoxy group which may be substituted with a hydroxy group, a (C1 to C4) alkoxy group, a sulfo group, or a carboxyl group include, for example, methoxy, ethoxy, n-propoxy, isopropoxy, n-butoxy, sec-butoxy, tert-butoxy, 2-hydroxyethoxy, 2-hydroxypropoxy, 3-hydroxypropoxy, methoxyethoxy, ethoxyethoxy, n-propoxyethoxy, isopropoxyethoxy, n-butoxyethoxy, methoxypropoxy, ethoxypropoxy, n-propoxypropoxy, isopropoxybutoxy, n-propoxybutoxy, 2-hydroxyethoxyethoxy, carboxymethoxy, 2-carboxyethoxy, 3-carboxypropoxy, 3-sulfopropoxy, 4-sulfobutoxy, and the like.

In $R^1$, $R^2$, and $R^6$ to $R^8$ in General Formula (1) and General Formula (2), examples of an acylamino group include, for example, acetylamino, propionylamino, butylylamino, isobutylylamino, benzoylamino, naphthoylamino, and the like.

In $R^3$ to $R^8$ in General Formula (1) and General Formula (2), examples of a (C1 to C4) alkyl group include methyl, ethyl, n-propyl, isopropyl, n-butyl, isobutyl, sec-butyl, tert-butyl, and the like.

In $R^5$ in General Formula (2), examples of a (C1 to C4) alkoxycarbonyl group include, for example, methoxycarbonyl, ethoxycarbonyl, n-propoxycarbonyl, isopropoxycarbonyl, n-butoxycarbonyl, sec-butoxycarbonyl, tert-butoxycarbonyl, and the like.

Preferable $R^1$ and $R^2$ in General Formula (1) are a hydrogen atom, a chlorine atom, a bromine atom, cyano, carboxyl, sulfo, sulfamoyl, N-methylaminosulfonyl, N-phenylaminosulfonyl, a phosphoric acid group, nitro, acetyl, benzoyl, ureide, methyl, methoxy, ethyl, ethoxy, propyl, propoxy, 2-hydroxyethoxy, 2-methoxyethoxy, 2-ethoxyethoxy, 3-sulfopropoxy, 4-sulfobutoxy, carboxymethoxy, 2-carboxyethoxy, acetylamino, benzoylamino, and the like, further preferably a hydrogen atom, a chlorine atom, cyano, sulfamoyl, acetyl, nitro, carboxyl, sulfo, and a phosphoric acid group, more preferably a hydrogen atom, carboxyl and sulfo.

For a combination of $R^1$ and $R^2$, a preferable combination is that $R^1$ is preferably carboxyl, sulfo, or a (C1 to C4) alkoxy group and $R^2$ is preferably a hydrogen atom or sulfo, and among them, a more preferable combination is that $R^1$ is carboxyl or sulfo and $R^2$ is a hydrogen atom. For a substitution position, a $NO_2$ group in Formula (1) may be at any of the ortho-position, the meta-position, or the para-position on a phenyl group, preferably the para-position or the ort-position. When $NO_2$ is at the para-position (at the 4-position), preferably $R^1$ is at the ortho-position (at the 2-position) and $R^2$ is at the meta-position (at the 5-position). In addition, when $NO_2$ is at the ortho-position (at the 2-position), preferably $R^1$ is at the para-position (at the 4-position), and sulfo is preferable as a substitution group. $R^2$ is, in this case, preferably a hydrogen atom.

Preferable $R^3$ and $R^4$ in General Formula (1) are a hydrogen atom, cyano, carboxyl, sulfo, nitro, methyl, methoxy, ethyl, ethoxy, propyl, propoxy, 2-hydroxyethoxy, 2-methoxyethoxy, 2-ethoxyethoxy, 3-sulfopropoxy, 4-sulfobutoxy, carboxymethoxy and 2-carboxyethoxy, more preferably a hydrogen atom, carboxyl, sulfo, nitro, methyl and methoxy, particularly preferably a hydrogen atom, sulfo and nitro. For a preferable combination, $R^3$ is sulfo or carboxyl and $R^4$ is a hydrogen atom, a (C1 to C4) alkyl group, a (C1 to C4) alkoxy group, sulfo, nitro, a halogen atom or carboxyl, more preferably $R^3$ is sulfo and $R^4$ is a hydrogen atom, sulfo, chlorine or carboxyl.

Preferable $R^5$ in General Formula (2) is cyano, carboxyl, methyl, ethyl, propyl, methoxycarbonyl, ethoxycarbonyl or phenyl, further preferably carboxyl, methyl, methoxycarbonyl or phenyl, particularly preferably carboxyl.

Each of preferable $R^6$, $R^7$ and $R^8$ in General Formula (2) is independently a hydrogen atom, a chlorine atom, a bromine atom, cyano, carboxyl, sulfo, nitro, methyl, methoxy, ethyl, ethoxy, 3-sulfopropoxy and acetylamino, further preferably a hydrogen atom, a chlorine atom, carboxyl, sulfo, nitro or methyl, more preferably a hydrogen atom, carboxyl, sulfo and nitro. For a combination of $R^6$, $R^7$ and $R^8$, a preferable combination is that $R^6$ is a hydrogen atom, a halogen atom or a (C1 to C4) alkyl group, preferably a hydrogen atom, $R^7$ is carboxyl, sulfo or nitro, preferably carboxyl or sulfo, and $R^8$ is a hydrogen atom, a halogen atom, carboxyl or sulfo.

Substitution positions of $R^6$, $R^7$ and $R^8$ are not particularly limited, but as a binding position to a pyrazole ring is the 1-position, the 2-, 4-, and 6-positions, or the 2-, 4- and 5-positions are preferable when all of $R^6$, $R^7$ and $R^8$ represent a group other than a hydrogen atom, and substitution positions of the 2- and 4-positions, the 2- and 5-positions, the 3- and 5-positions and the like are preferable when either of $R^6$ and $R^8$ represents a hydrogen atom and the other represents a group other than a hydrogen atom.

In General Formula (2), as a phenyl group substituted with $R^6$, $R^7$ and $R^8$, p-sulfophenyl, 2,5-disulfophenyl, 3,5-dicarboxyphenyl or the like is preferable.

Preferable compounds in General Formula (1) include compounds wherein $R^1$ is carboxyl, sulfo or a (C1 to C4) alkoxy group, preferably carboxyl or sulfo, $R^2$ is a hydrogen atom or sulfo, preferably a hydrogen atom, n is 0 or 1, preferably 1, $R^3$ is sulfo or carboxyl, preferably sulfo, and $R^4$ is a hydrogen atom, a (C1 to C4) alkyl group, a (C1 to C4) alkoxy-group, sulfo, nitro, a halogen atom or carboxyl, preferably a hydrogen atom, sulfo, chlorine or carboxyl, and $R^5$ in Formula (2) is cyano, carboxyl, a (C1 to C4) alkyl group, a (C1 to C4) alkoxy group, a (C1 to C4) alkoxycarbonyl group or phenyl, preferably carboxyl, $R^6$ is a hydrogen atom, a halogen atom or a (C1 to C4) alkyl group, preferably a hydrogen atom, $R^7$ is carboxyl, sulfo or nitro, preferably carboxyl or sulfo, $R^8$ is a hydrogen atom, a halogen atom, carboxyl or sulfo, preferably a hydrogen atom or carboxyl, more preferably compounds wherein $R^1$ to $R^4$ are the same groups as mentioned above and $R^5$ in Formula (2) is carboxyl and a phenyl group substituted with $R^6$, $R^7$ and $R^8$ is p-sulfophenyl, 2,5-disulfophenyl or 3,5-dicarboxyphenyl.

The salt of the compounds shown in above Formulas (1), (3) and (5) is an inorganic or organic cation salt. Examples of an inorganic salt include an alkali metal salt, an alkaline earth metal salt and an ammonium salt, preferably salts of lithium, sodium or potassium and an ammonium salt, and as an organic cation salt, for example, the salt shown in above Formula (6) is included, but not limited thereto.

Examples of an alkyl group of $Z^1$, $Z^2$, $Z^3$ and $Z^4$ in General Formula (6) include methyl, ethyl, n-propyl, isopropyl, n-butyl, isobutyl, sec-butyl and tert-butyl, and the like, examples of a hydroxyalkyl group include a hydroxy-(C1 to C4) alkyl group such as hydroxymethyl, hydroxyethyl, 3-hydroxypropyl, 2-hydroxypropyl, 4-hydroxybutyl, 3-hydroxybutyl and 2-hydroxybutyl, and examples of a hydroxyalkoxyalkyl group include a hydroxy(C1 to C4) alkoxy-(C1 to C4) alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl and 2-hydroxyethoxybutyl, among which a hydroxyethoxy-(C1 to C4)alkyl group is preferable. As particularly preferable ones, a hydrogen atom; methyl; a hydroxy-(C1 to C4)alkyl group such as hydroxymethyl, hydroxyethyl, 3-hydroxypropyl, 2-hydroxypropyl, 4-hydroxybutyl, 3-hydroxybutyl, 2-hydroxybutyl; and a hydroxyethoxy-(C1 to C4)alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl, 2-hydroxyethoxybutyl are included.

Specific examples of $Z^1$, $Z^2$, $Z^3$ and $Z^4$ in General Formula (6) will be shown in (Table 1).

TABLE 1

| Compound No. | $Z^1$ | $Z^2$ | $Z^3$ | $Z^4$ |
|---|---|---|---|---|
| 1-1 | H | —C2H4OH | —C2H4OH | —C2H4OH |
| 1-2 | CH3 | —C2H4OH | —C2H4OH | —C2H4OH |
| 1-3 | H | —CH2CH(OH)CH3 | —CH2CH(OH)CH3 | —CH2CH(OH)CH3 |
| 1-4 | CH3 | —CH2CH(OH)CH3 | —CH2CH(OH)CH3 | —CH2CH(OH)CH3 |
| 1-5 | H | —C2H4OH | H | —C2H4OH |
| 1-6 | CH3 | —C2H4OH | H | —C2H4OH |
| 1-7 | H | —CH2CH(OH)CH3 | H | —CH2CH(OH)CH3 |
| 1-8 | CH3 | —CH2CH(OH)CH3 | H | —CH2CH(OH)CH3 |
| 1-9 | CH3 | —C2H4OH | CH3 | —C2H4OH |
| 1-10 | CH3 | —CH2CH(OH)CH3 | CH3 | —CH2CH(OH)CH3 |

The azo compounds of the present invention shown by General Formula (1), (3) and (5) can be synthesized, for example, in the following method. Structural formulas of a compound in each step are represented in a free acid form. That is, the following General Formula (7)

[Formula 7]

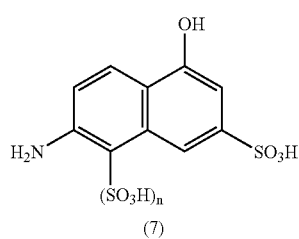

(7)

(wherein, n has the same meaning as in General formula (1)) and p-toluenesulfonylchloride are reacted in the presence of alkaline to obtain a compound represented by Formula (8)

[Formula 8]

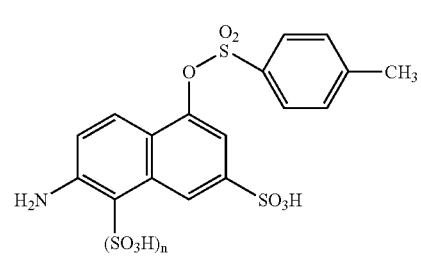

(8)

(wherein, n has the same meaning described above), which compound is diazotized in a conventional manner, and then subjected to a coupling reaction with 4-amino-5-naphtol-1,7-disulfonic acid under acidic conditions to produce a compound represented by Formula (9)

[Formula 9]

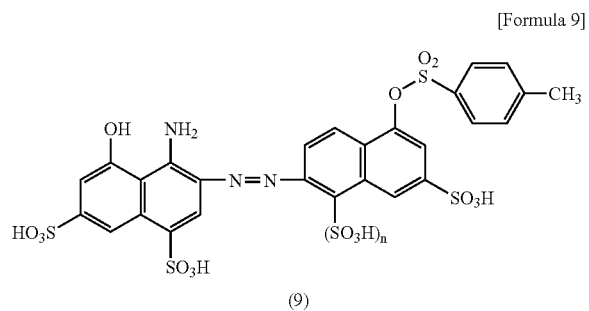

(9)

(wherein, n has the same meaning described above), which is then subjected to a coupling reaction with a compound obtained by diazotizing a compound represented by Formula (10)

[Formula 10]

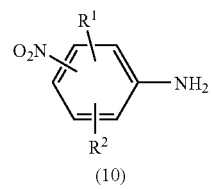

(10)

(wherein, $R^1$ and $R^2$ have the same meanings as in General Formula (1)) in a conventional manner to obtain a compound represented by Formula (11)

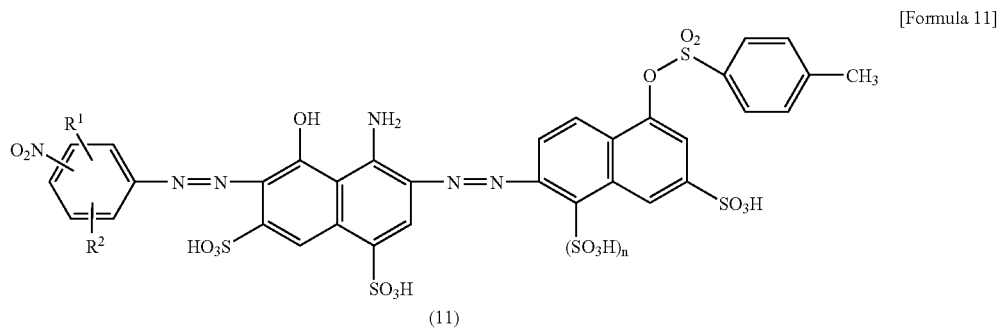

[Formula 11]

(wherein, $R^1$, $R^2$ and n have the same meanings described above), which compound is then hydrolyzed under alkaline conditions to obtain a compound represented by Formula (12)

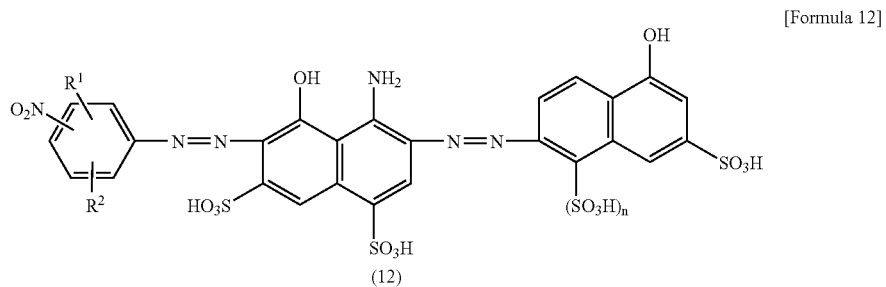

[Formula 12]

(wherein, $R^1$, $R^2$ and n have the same meanings described above). Aside from this, a compound obtained by diazotizing a compound represented by General Formula (13)

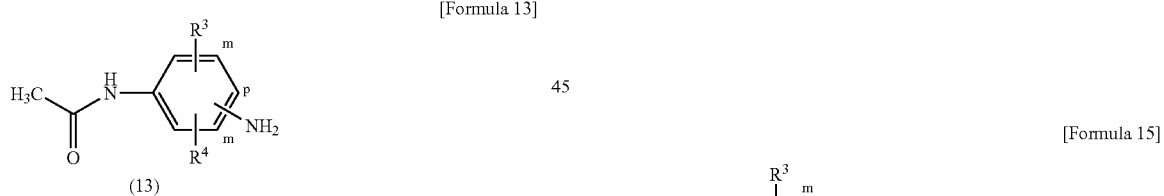

[Formula 13]

(wherein, $R^3$ and $R^4$ have the same meanings as in General Formula (1)) in a conventional manner is subjected to a coupling reaction with a compound represented by General Formula (14)

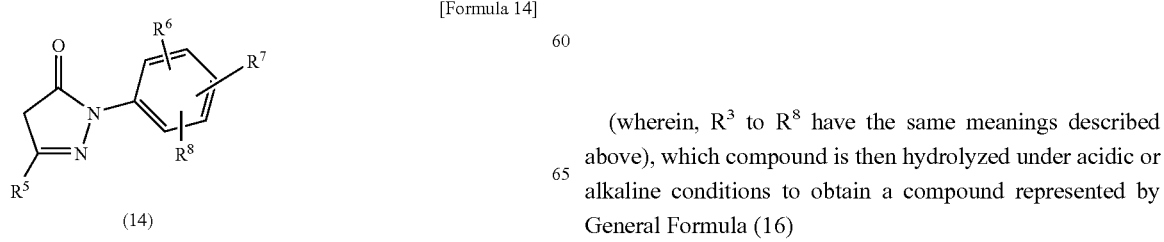

[Formula 14]

(wherein $R^5$ to $R^8$ have the same meanings as in General Formula (1) and (2)) to obtain a compound represented by General Formula (15)

[Formula 15]

(wherein, $R^3$ to $R^8$ have the same meanings described above), which compound is then hydrolyzed under acidic or alkaline conditions to obtain a compound represented by General Formula (16)

[Formula 16]

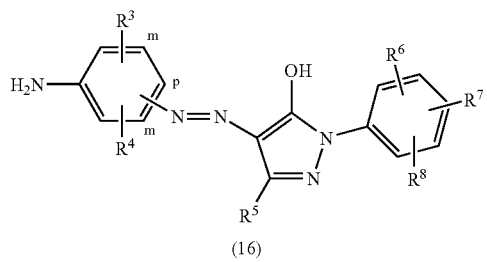

(16)

(wherein, $R^3$ to $R^8$ have the same meanings described above). This is diazotized in a conventional manner, and then subjected to a coupling reaction with a compound of General Formula (12) to obtain an azo compound of the present invention represented by General Formula (1) or a salt thereof.

As appropriate examples of a compound shown by General Formula (1), not particularly limited, but for specific examples, compounds having the following structures are included.

TABLE 2

| Compound No. | Structural Formula |
|---|---|
| 1 | |
| 2 | |

TABLE 2-continued

| Compound No. | Structural Formula |
|---|---|
| 3 | (chemical structure) |
| 4 | (chemical structure) |
| 5 | (chemical structure) |

TABLE 2-continued
| Compound No. | Structural Formula |
| --- | --- |
| 6 | 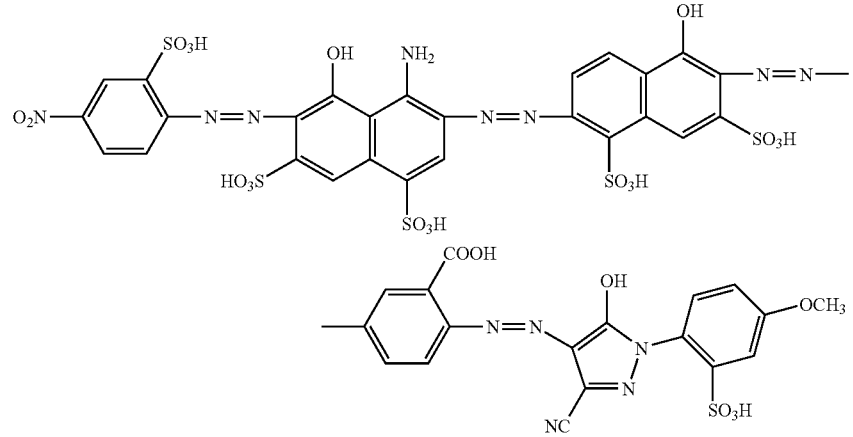 |
| 7 | 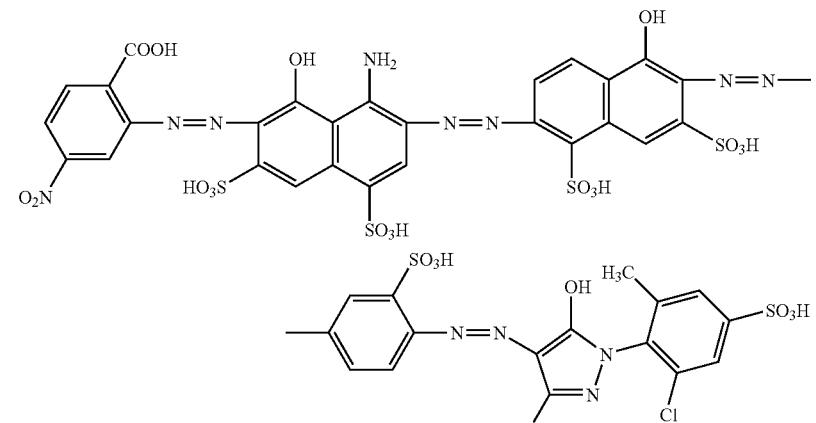 |
TABLE 3
| Compound No. | Structural Formula |
| --- | --- |
| 8 | 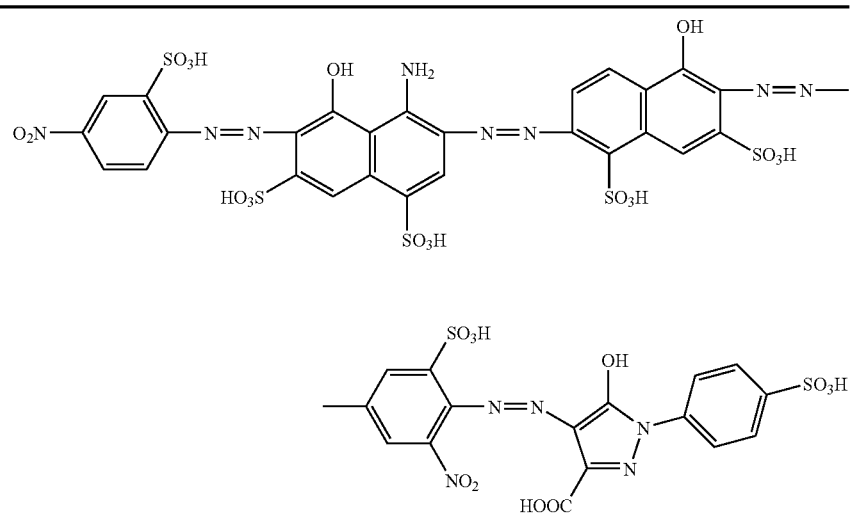 |

TABLE 3-continued

| Compound No. | Structural Formula |
|---|---|
| 9 | (structure) |
| | (structure) |
| 10 | (structure) |
| | (structure) |
| 11 | (structure) |
| | (structure) |

TABLE 3-continued
| Compound No. | Structural Formula |
|---|---|
| 12 | 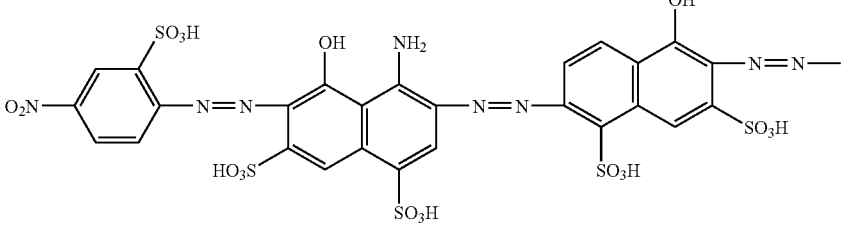 |
| 13 | 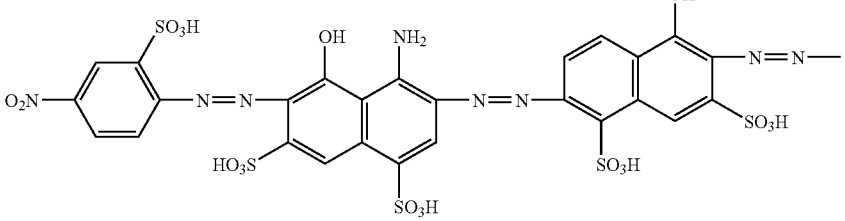 |
| 14 | 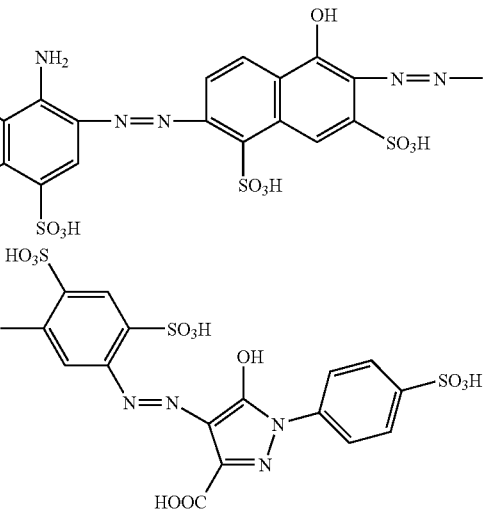 |

TABLE 4
| Compound No. | Structural Formula |
|---|---|
| 15 | 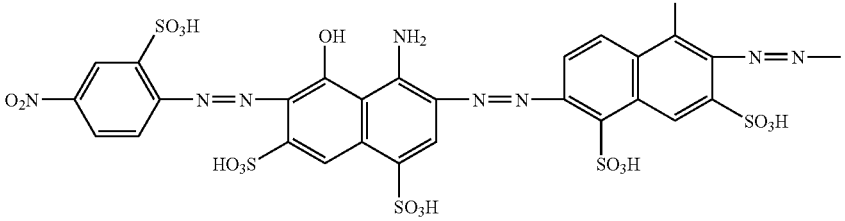 |
| 16 | 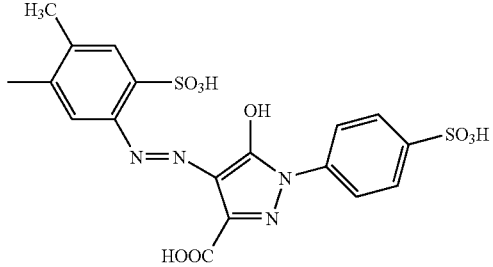 |
| 17 | 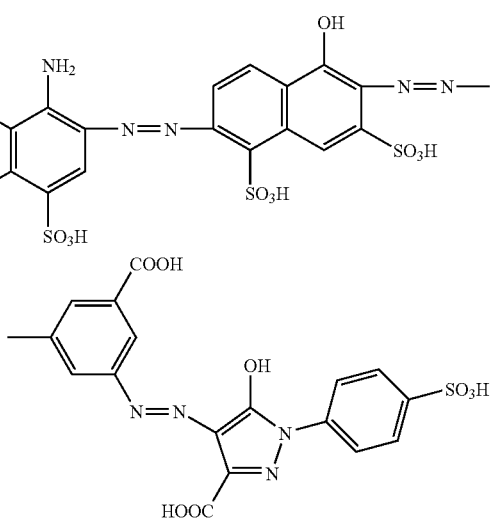 |

TABLE 4-continued
| Compound No. | Structural Formula |
|---|---|
| 18 | 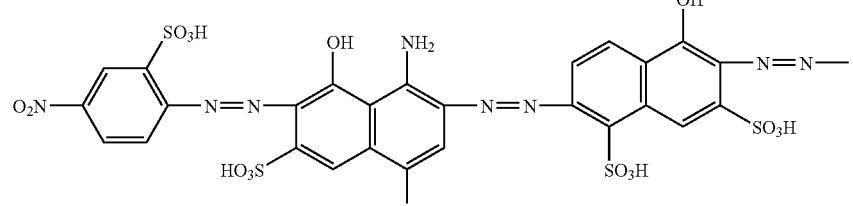 |
| 19 | 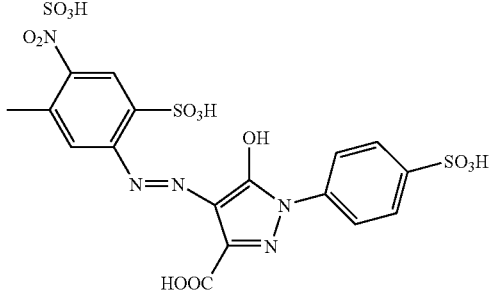 |
| 20 | 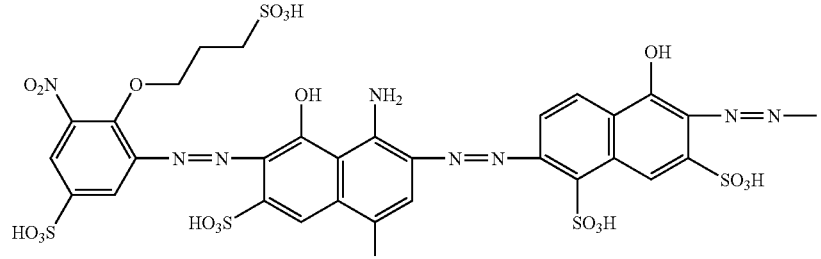 |

TABLE 5

| Compound No. | Structural Formula |
|---|---|
| 21 | |
| 22 | |
| 23 | |

TABLE 5-continued
| Compound No. | Structural Formula |
|---|---|
| 24 | 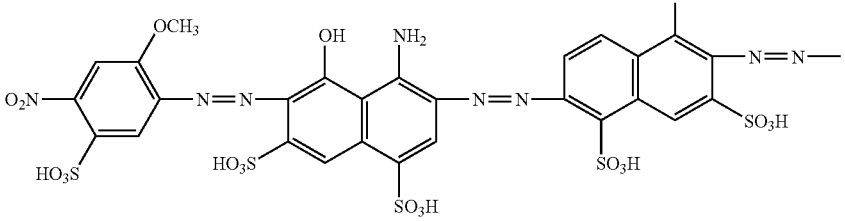 |
| 25 | 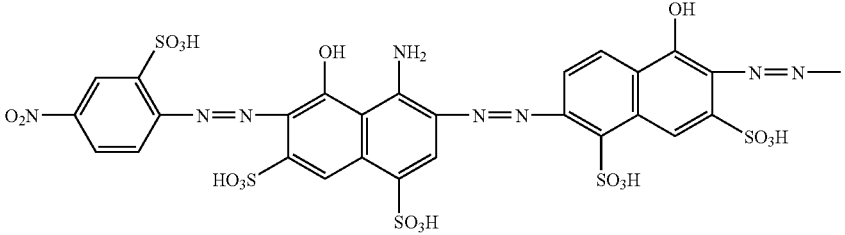 |
| 26 | 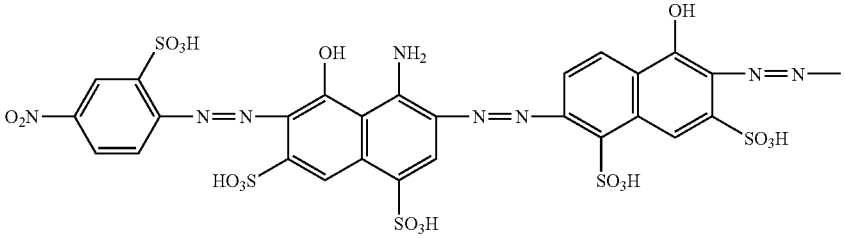 |

TABLE 5-continued

| Compound No. | Structural Formula |
|---|---|
| 27 | 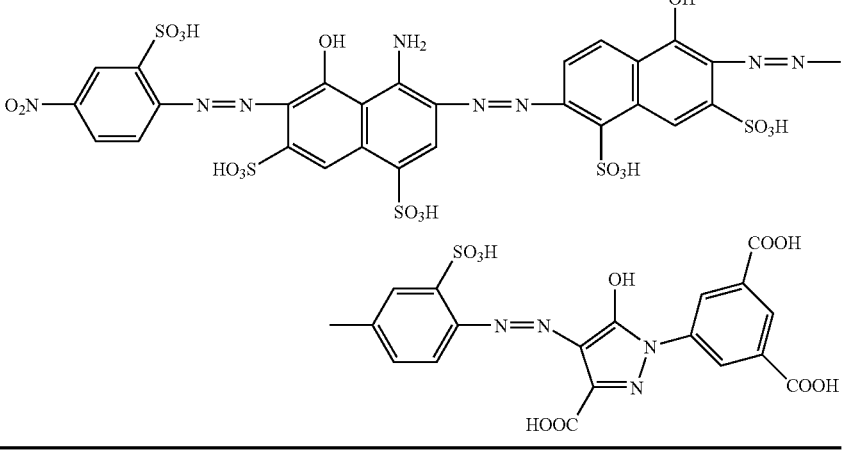 |

Method of producing the compound of Formula (1) of the present invention will be more specifically explained.

Esterification reaction of the compound of Formula (7) and p-toluenesulphonylchloride is carried out by a known method per se, favorably conducted in an aqueous or aqueous organic medium, for example, at a temperature of 20 to 100° C., preferably 30 to 80° C., and at neutral to alkaline pH value. It is preferably carried out at neutral to weakly alkaline pH value, for example, at pH 7 to 10. Adjustment of this pH value is carried out by the addition of a base. As a base, for example, a hydroxide of an alkali metal such as lithium hydroxide and sodium hydroxide, a carbonate salt of an alkali metal such as lithium carbonate, sodium carbonate and potassium carbonate, or an acetate salt such as sodium acetate can be used. A compound of Formula (7) and p-toluenesulfonyl chloride are used in nearly stoichiometric amounts.

Diazotization of a compound of Formula (8) is also carried out by a known method per se, for example, in an inorganic acid medium, for example, at a temperature of −5 to 30° C., preferably 5 to 15° C., using a nitrite salt, for example, a nitrite salt of an alkali metal such as sodium nitrite. Coupling of a diazotized compound of the compound of Formula (8) and 4-amino-5-naphtol-1,7-disulfonic acid is carried out under known conditions per se. It is favorable to conduct in an aqueous or aqueous organic medium, at a temperature of −5 to 30° C., preferably 5 to 25° C., and at acidic to neutral pH value. It is preferably carried out at acidic to weakly acidic pH value, for example, at pH 1 to 4. A base is used for neutralization of acids produced in the progress of the reaction, and as the base, for example, an alkali metal hydroxide such as lithium hydroxide and sodium hydroxide, an alkali metal carbonate salt such as lithium carbonate, sodium carbonate and potassium carbonate, an acetate salt such as sodium acetate, an ammonia or an organic amine and the like can be used. A compound of Formula (8) and 4-amino-5-naphtol-1, 7-disulfonic acid are used in nearly stoichiometric amounts.

Diazotization of the compound of Formula (10) is also carried out by a known method per se, for example, in an inorganic acid medium, for example, at a temperature of −5 to 30° C., preferably 0 to 15° C., using a nitrite salt, for example, an alkali metal nitrite salt such as sodium nitrite. Coupling of a diazotized compound of the compound of Formula (10) and a compound of Formula (9) is also carried out under known conditions per se. It is favorable to conduct in an aqueous or aqueous organic medium, for example, at a temperature of −5 to 30° C., preferably 10 to 25° C., and at weakly acidic to alkaline pH value. It is preferably carried out at weakly acidic to weakly alkaline pH value, for example, at pH 5 to 10, and adjustment of the pH value is carried out by the addition of a base.

As a base, for example, an alkali metal hydroxide such as lithium hydroxide and sodium hydroxide, an alkali metal carbonate salt such as lithium carbonate, sodium carbonate and potassium carbonate, an acetate salt such as sodium acetate, or ammonia or an organic amine and the like can be used. The compounds of Formula (9) and (10) are used in nearly stoichiometric amounts.

Production of a compound of General Formula (12) by hydrolyzing a compound of Formula (11) is also carried out by a known method per se. Favorable is a method of heating in an aqueous alkaline medium, which is carried out, for example, by the addition of sodium hydroxide or potassium hydroxide into a solution comprising a compound of General Formula (11) to adjust the pH at 9.5 or higher, followed by heating, for example, at a temperature of 20 to 150° C., preferably 30 to 100° C. The pH value of the reaction solution at this time is preferably maintained at 9.5 to 11.5. Adjustment of this pH value is carried out by the addition of a base. The bases mentioned above can be used.

Diazotization of a compound of Formula (13) is also carried out by a known method per se, for example, in an inorganic acid medium, for example, at a temperature of −5 to 30° C., preferably 0 to 15° C., using a nitrite salt, for example, an alkali metal nitrite salt such as sodium nitrite. Coupling of a diazotized compound of the compound of Formula (13) and a compound of Formula (14) is also carried out under known conditions per se. It is favorable to conduct in an aqueous or aqueous organic medium, for example, at a temperature of 5 to 40° C., preferably 10 to 25° C., and at weakly acidic to alkaline pH value. It is preferably carried out at neutral to alkaline pH value, for example, at pH 6 to 10, and adjustment of the pH value is carried out by the addition of a base. As a base, for example, an alkali metal hydroxide such as lithium hydroxide and sodium hydroxide, an alkali metal carbonate salt such as lithium carbonate, sodium carbonate and potassium carbonate, an acetate salt such as sodium acetate, or ammonia or an organic amine and the like can be used. The compounds of Formula (13) and (14) are used in nearly stoichiometric amounts.

Production of a compound of General Formula (16) by hydrolyzing a compound of Formula (15) is also carried out by a known method per se. Favorable is a method of heating in an aqueous acidic or alkaline medium, which is carried out, for example, by the addition of hydrochloric acid or sulfuric acid into a solution comprising a compound of General Formula (15) to adjust the pH at 1.0 or lower or at 13 or higher, followed by heating, for example, at a temperature of 20 to 150° C., preferably 40 to 100° C. The pH value of the reaction solution at this time is preferably maintained at 1.0 or lower or at 13 or higher. Adjustment of this pH value is carried out by the addition of an acid or a base. The acids and bases mentioned above can be used.

Diazotization of a compound of Formula (16) is also carried out by a known method per se, for example, in an inorganic acid medium, for example, at a temperature of −5 to 30° C., preferably 5 to 25° C., using a nitrite salt, for example, an alkali metal nitrite salt such as sodium nitrite. Coupling of a diazotized compound of the compound of Formula (13) and a compound of Formula (12) is also carried out under known conditions per se. It is favorable to conduct in an aqueous or aqueous organic medium, for example, at a temperature of 5 to 30° C., preferably 10 to 25° C., and at weakly acidic to alkaline pH value. It is preferably carried out at neutral to alkaline pH value, for example, at pH 6 to 10, and adjustment of the pH value is carried out by the addition of a base. As a base, for example, an alkali metal hydroxide such as lithium hydroxide and sodium hydroxide, an alkali metal carbonate salt such as lithium carbonate, sodium carbonate and potassium carbonate, an acetate salt such as sodium acetate, or ammonia or an organic amine and the like can be used. The compounds of Formula (12) and (16) are used in nearly stoichiometric amounts.

An azo compound according to the present invention shown in General Formula (1), (3) or (5) or a salt thereof (hereinafter, a compound or a salt thereof is referred to as a compound for simplicity unless otherwise specified), after a coupling reaction, can be isolated in a free acid form by the addition of a mineral acid, and then washed by water or acidified water to eliminate inorganic salt. Thus obtained acidic-type coloring matter having a low percentage salt content can be neutralized with an optional inorganic or organic base in an aqueous medium to make a corresponding salt solution. Examples of an inorganic base include, for example, a hydroxide of an alkali metal such as lithium hydroxide, sodium hydroxide and potassium hydroxide, ammonium hydroxide, a carbonate salt of an alkali metal such as lithium carbonate, sodium carbonate and potassium carbonate, and the like, and examples of an organic base include, an organic amine, for example, an alkanolamine such as diethanolamine and triethanolamine, and the like, however not limited thereto.

Thus obtained compound of the present invention is useful as a black dye, and can be made into a fluid composition for use of dyeing, preferably an aqueous composition, by dissolving it in a liquid medium such as water or aqueous solvent (a mixed solvent of water and water-miscible solvent) and adding an additive agent to be used for dyeing as required. Said composition can dye materials including cellulose. Furthermore, it can dye other materials having a carbonamide bond, and be used for a wide range of dyeing leather, textile and paper. As a preferable one of said composition, an ink composition can be included, particularly preferably an ink composition to be used for ink-jet printing.

A reaction solution containing an azo compound of the present invention shown by the above General Formula (1), (3) or (5) can be directly used to produce an ink composition. Otherwise, this solution can be first subjected to drying, for example, spray drying to isolate the azo compound; or subjected to salting out with inorganic salts such as sodium chloride, potassium chloride, calcium chloride and sodium sulfate; aciding out with mineral acid such as hydrochloric acid, sulfuric acid and nitric acid; or aciding-salting out which is a combination of the above described salting-out and aciding-out, to separate an azo compound of the present invention, and then if required, followed by desalting process, it can be used for an ink composition.

An ink composition according to the present invention is an aqueous composition, where the main medium is water comprising usually 0.1 to 20 mass %, preferably 1 to 10 mass %, and more preferably 2 to 8 mass % of an azo compound of the present invention shown by General Formula (1), (3) or (5). The ink composition according to the present invention, if required, may comprise water-soluble organic solvent of, for example, 0 to 30 mass %, and ink preparation agent of, for example, 0 to 5 mass %. In addition, the ink composition, in view of improving storage stability, has preferably pH 6 to 10, more preferably pH 7 to 10. The ink composition has preferably surface tension of 25 to 70 mN/m, more preferably 25 to 60 mN/m. Furthermore, the ink composition has preferably viscosity of not higher than 30 mPa·s, more preferably not higher than 20 mPa·s.

An ink composition according to the present invention is one obtained by dissolving an azo compound shown by the above General Formula (1), (3) or (5) in water or a mixture of water-soluble organic solvent (water-miscible organic solvent) and water, if required, by the addition of an ink preparation agent. The ink composition according to the present invention preferably has about pH 5 to 11. When this ink composition is used as an ink for an ink-jet printer, it is preferable to use a compound of the present invention containing less inorganic substance such as a chloride of metal cation, a sulfate salt and the like, and the content is, for example, not more than about 1 mass % (based on the coloring matter) only as guide. To produce a compound of the present invention containing less inorganic substances, for example, desalting treatment may be conducted by a method such as an ordinary reverse osmosis method, a method by which a dried material or a wet cake of a compound of the present invention is stirred in a mixed solvent of an alcohol such as methanol and water, filtered, and dried, a method by which a wet cake is dissolved in water and crystallized with water-soluble alcohol such as methanol or ethanol, and the like.

A water-soluble organic solvent which can be used in preparation of the above ink composition includes, for example, a (C1 to C4) alkanol such as methanol, ethanol, propanol, isopropanol, butanol, isobutanol, sec-butanol and tert-butanol; a carboxylic amide such as N,N-dimethylformamide or N,N-dimethylacetamide; a lactam such as 2-pyrrolidone and N-methylpyrrolidine-2-one; cyclic ureas such as 1,3-dimethylimidazolidine-2-one or 1,3-dimethylhexahydropyrimide-2-one; a ketone or a ketoalcohol such as acetone, methylethylketone and 2-methyl-2-hydroxypentane-4-one; a cyclic ether such as tetrahydrofuran and dioxane; a monomer, oligomer or polyalkylene glycol or thio glycol having (C2 to C6) alkylene units such as ethylene glycol, 1,2-propylene glycol, 1,3-propylene glycol, 1,2-butylene glycol, 1,4-butylnene glycol, 1,6-hexylene glycol, diethylene glycol, triethylene glycol, tetraethylene glycol, dipropylene glycol, polyethylene glycol, polypropylene glycol, thio diglycol and dithio diglycol; a polyol (triol) such as glycerin, and hexane-1,2,6-triol; a (C1 to C4) alkyl ether of a polyhydric alcohol such as ethylene glycol monomethyl ether or ethylene glycol monoethyl ether, diethylene glycol monomethyl ether or diethylene glycol monoethyl ether or triethylene glycol monomethyl ether or triethyleneglycol monoethyl ether; gamma-butylolactone; dimethylsulfoxide; and the like. These organic solvents may be used alone or in a combination of two or more kinds thereof.

In preparing the above ink composition, an ink preparation agent to be used if required includes, for example, an antiseptic and fungicide, a pH modifier, a chelating agent, an antirust agent, a water-soluble ultraviolet absorber, a water-soluble polymer, a dye-dissolving agent, an antioxidant and a surfactant.

The antiseptic and fungicide includes a compound of, for example, an organic sulfur base, an organic nitrogen sulfur base, an organic halogen base, a haloallylsulfone base, an iodopropargyl base, an N-haloalkylthio base, a nitrile base, a pyridine base, an 8-oxyquinoline base, a benzothiazole base, an isothiazoline base, a dithiol base, a pyridineoxide base, a nitropropane base, an organotin base, a phenol base, a quaternary ammonium salt base, a triazine base, a thiazine base, an anilide base, an adamantane base, a dithiocarbamate base, a brominated indanone base, a benzylbromoacetate base and an inorganic salt base. The compound of an organic halogen base includes, for example, sodium pentachlorophenol, the compound of a pyridineoxide base includes, for example, sodium 2-pyridinethiol-1-oxide, and the compound of an inorganic salt base includes, for example, anhydrous sodium acetate, and the compound of an isothiazoline base includes, for example, 1,2-benzisothiazoline-3-one, 2-n-octyl-4-isothiazoline-3-one, 5-chloro-2-methyl-4-isothiazoline-3-one, 5-chloro-2-methyl-4-isothiazoline-3-one magnesium chloride, 5-chloro-2-methyl-4-isothiazoline-3-one calcium chloride, 2-methyl-4-isothiazoline-3-one calcium chloride and the like.

Other antiseptic and fungicides include sodium sorbate, sodium benzoate, and the like.

As a pH modifier, any substance can be used as long as it can control the pH of an ink in the range of, for example, 5 to 11, without impairing an ink to be formulated. An example of the pH modifier includes an alkanolamine such as diethanolamine, triethanolamine and N-methyldiethanolamine; a hydroxide of an alkali metal such as lithium hydroxide, sodium hydroxide and potassium hydroxide; an ammonium hydroxide (ammonia); a carbonate salt of an alkali metal such as lithium carbonate, sodium carbonate, sodium hydrogencarbonate and potassium carbonate; potassium acetate; an inorganic base such as sodium silicate and disodium phosphate; and the like.

The chelating agent includes, for example, sodium ethylenediamine tetraacetate, sodium nitrilo triacetate, sodium hydroxyethylethylenediamine triacetate, sodium diethylenetriamine pentaacetate, sodium uracil diacetate and the like.

The antirust agent includes, for example, an acidic sulfite salt, sodium thiosulfate, ammonium thioglycolate, diisopropyl ammonium nitrite, pentaerythritol tetranitrate, dicyclohexyl ammonium nitrite and the like.

The water-soluble ultraviolet absorber includes, for example, a sulfonated benzophenone-based compound, a benzotriazole-based compound, a salicyclic acid-based compound, a cinnamic acid-based compound and a triazine-based compound.

The water-soluble polymer includes polyvinyl alcohol, a cellulose derivative, a polyamine, a polyimine, and the like.

The dye-dissolving agent includes, for example, ε-caprolactam, ethylene carbonate, urea and the like.

As antioxidant, for example, various organic or metal complex-based fading inhibitors can be used. The above organic fading inhibitors include hydroquinones, alkoxyphenols, dialkoxyphenols, phenols, anilines, amines, indans, chromans, alkoxyanilines, heterocycles and the like.

The surfactant includes known surfactants such as an anionic, cationic and nonionic surfactant. The anionic surfactant includes an alkyl sulfonic acid, alkyl carboxylate, α-olefin sulfonate, polyoxyethylene alkyl ether acetate, N-acylamino acid and a salt thereof, N-acylmethyltaurine salt, alkyl sulfate-polyoxyalkyl ether sulfate, alkyl sulfate-polyoxyethylenealkyl ether phosphate, rosin acid soap, caster oil sulfate, lauryl alcohol sulfate, alkylphenol-type phosphoric ester, alkyl-type phosphonate ester, alkylallyl sulfonate, diethylsulfo succinate, diethylhexylsulfo succinic acid-dioctylsulfo succinate and the like. The cationic surfactant includes a 2-vinylpyridine derivative, a poly 4-vinylpyridine derivative and the like. The ampholytic surfactant includes lauryidimethylamino acetic acid betaine, 2-alkyl-N-carboxymethyl-N-hydroxyethylimidazolinium betaine, coconut oil fatty acid amide propyldimethylamino acetic acid betaine, polyoctylpolyaminoethylglycine and others such as an imidazoline derivative. The nonionic surfactant includes ethers such as polyoxyethylene nonyl phenyl ether, polyoxyethylene octyl phenyl ether, polyoxyethylene dodecyl phenyl ether, polyoxyethylene oleyl ether, polyoxyethylene lauryl ether and polyoxyethylene alkyl ether; esters such as polyoxyethylene oleic acid, polyoxyethylene oleate, polyoxyethylene distearate, sorbitan laurate, sorbitan monostearate, sorbitan monooleate, sorbitan sesquiorate, polyoxyethylene monooleate and polyoxyethylene stearate; and acetylene glycols such as 2,4,7,9-tetramethyl-5-decyne-4,7-diol, 3,6-dimethyl-4-octyne-3,6-diol and 3,5-dimethyl-1-hexyne-3-ol (for example, Surfynol 104, 105, 82, 465, and Olfine STG from Nissin Chemical Industry Co., Ltd.). These surfactants are used alone or in mixture thereof.

An ink composition according to the present invention is obtained by mixing and stirring the above ingredients in arbitrary order. Thus obtained ink composition may be filtered with a membrane filter or the like to remove impurities. To adjust black tones, other coloring matter having various hues may be mixed. In that case, besides the azo compound of the present invention shown by the general Formula (1), (3) and (5), coloring matter of black having other hues, yellow, magenta, cyan and other colors can be used.

An ink composition according to the present invention can be used in various fields, and is suitable for a water-base ink for writing, a water-base printing ink, an information recording ink, and the like, particularly preferably for an ink for ink-jet printing comprising said ink composition, and suitably used in an ink-jet recording method described later.

A method of ink-jet recording (same as to coloring) according to the present invention will be explained hereinafter. A method of ink-jet recording according to the present invention is characterized by recording by applying an ink for ink-jet recording comprising said ink composition to record-receiving materials by using an ink-jet printer. In the method of ink-jet recoding according to the present invention, recording is conducted by spraying the above ink for ink-jet recording to record-receiving materials (including coloring receiving materials and image receiving materials) using an ink-jet printer. An ink nozzle and the like to be used in this case are not especially limited and can be selected appropriately according to the purpose, and known methods such as an electric charge controlling method to discharge ink utilizing static induction force, a drop-on-demand method (pressure pulse method) to make use of vibration pressure of piezoelectric elements, an acoustic ink-jet method to discharge ink by radiation pressure of acoustic beams converted from electric signals and by irradiation of ink, a thermal ink-jet method (Bubble Jet (registered trademark)) to make use of pressure of bubbles generated by heating ink, and the like can be used. The above ink-jet recording method also includes a method for injecting a number of tiny droplets of a low concentration ink called a photo ink, a method for improving image quality using multiple inks having substantially the same hue and different concentration, and a method for using a colorless and transparent ink.

An ink-jet printer in the present invention is equipped with an ink-container filled with the above ink composition, and used for the above method of ink-jet recording.

The colored object (including the recorded object) according to the present invention is a colored object with the above compound of the present invention or a composition comprising thereof, for example, an ink composition, more preferably one colored by an ink-jet printer using the ink composition according to the present invention. For color-receiving materials (image-receiving materials), materials including the above cellulose can be dyed. Furthermore, other materials having a carbonamide bond can be dyed, so, it is possible to dye widely leather, textile and paper. For example, sheet for information transmission such as paper, film and the like, textile or cloth (cellulose, nylon, wool and the like), leather, substrates for color filter and the like are included. Sheet for information transmission includes preferably surface-treated one, specifically one provided an ink receiving layer on the substrate of paper, synthetic paper, film and the like. An ink receiving layer is provided, for example, by impregnating or coating cationic polymer on the above substrate, or by coating white inorganic particles such as porous silica, aluminasol or special ceramics and the like which can absorb coloring matter in the ink on the surface of the above substrate together with a hydrophilic polymer such as polyvinylalcohol, polyvinylpyrrolidone and the like. Such ones as provided with an ink receiving layer are usually called paper (film) for exclusive ink-jet use, glossy paper (film) and the like, and available as typical commercial items, for example, Pictorico (manufactured by Asahi Glass Co., Ltd.); Professional Photopaper, Super Photopaper, and Mat Photopaper (all manufactured by Canon Inc.), a paper for PM photograph (glossy), a paper for PM mat (both manufactured by SEIKO-EPSON Co., Ltd.); Premium Plus Photo Paper, Premium Glossy Film and Photo Paper (all manufactured by Hewlett Packard Company, Japan); PhotoLikeQP (manufactured by KONICA MINOLTA Japan); and the like. In addition, naturally plain paper can be used.

An azo compound of the present invention is excellent in water-solubility, and an ink composition comprising this azo compound of the present invention does not appear crystal deposition, change in physical property, nor color change and the like after storage for a long period of time, and exhibit favorable storage stability. And a black ink liquid (composition) for recording which comprises an azo compound of the present invention is used for ink-jet recording and for writing tools, and when a printing is recorded on a plain paper and a paper exclusive use for ink-jet with said an ink liquid, an obtained recorded object exhibits a black color with high printing density, and are excellent in ozone fastness, light fastness, moisture fastness and color rendering properties.

EXAMPLES

Hereinafter, the present invention will be more specifically explained by Examples, but the present invention should not be limited thereto. In this connection, "part" and "%" in the specification are based on mass unless otherwise specified.

Example 1

(1) 20.1 parts of 2-amino-5-naphthol-1,7-disulfonic acid and 12.6 parts of p-toluenesulfonylchloride were subjected to reaction at pH 8.0 to 8.5, at 70° C. for 1 hour, followed by salting out in acidic condition and filtering to obtain the compound of Formula (17), and 28.4 parts of the compound was then dissolved in 300 parts of water while adjusting the pH at 6.0 to 8.0 with sodium carbonate, and after adding 18.7 parts of 35% hydrochloric acid, diazotized by the addition of 10.7 parts of 40% aqueous solution of sodium nitrite, at 0 to 5° C.

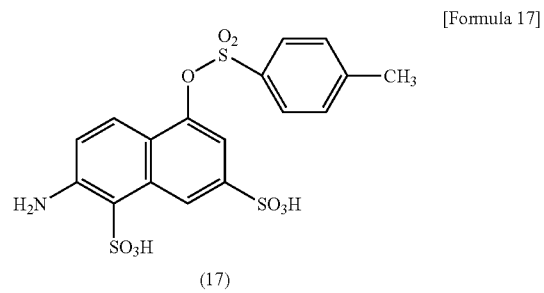

[Formula 17]

(17)

To this diazo suspension was added a solution of 19.1 parts of 4-amino-5-hydroxynaphthalene-1,7-disulfonic acid suspended in 200 parts of water, followed by stirring for 12 hours while maintaining the pH of the solution at 2.4 to 2.8 with sodium carbonate, at 10 to 20° C. After stirring, adjusting the pH at 7.0 to 8.5 with sodium carbonate to dissolve, a solution containing a monoazo compound of Formula (18) was obtained.

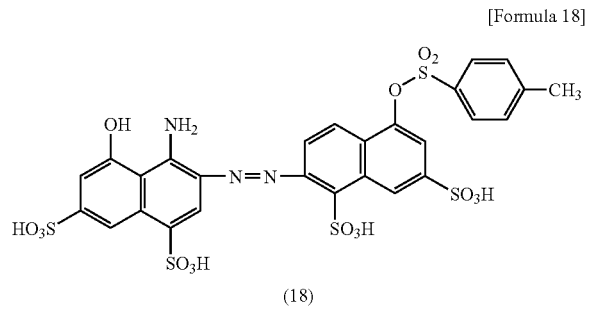

[Formula 18]

(18)

(2) In 150 parts of water 14.4 parts of sodium 4-nitroaniline-2-sulfonate was dissolved, and diazotized by the addition of 18.8 parts of 35% hydrochloric acid and 10.6 parts of 40% aqueous solution of sodium nitrite at 0 to 5° C. thereto. This diazo suspension was added dropwise into a solution containing a mono azo compound of Formula (18) obtained by the above reaction while maintaining the pH of the solution at 8.0 to 9.0 with sodium carbonate at 10 to 20° C. After completion of the dropwise addition, stirring at pH 8.0 to 9.0, at 15 to 30° C. for 2 hours, followed by salting out by the addition of sodium chloride and filtering, a wet cake containing a compound of Formula (19) was obtained.

[Formula 19]

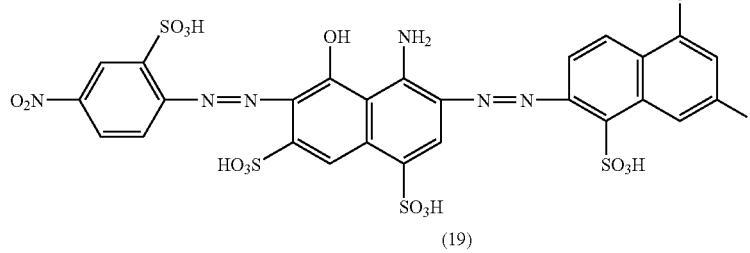

(19)

The above obtained wet cake was dissolved in 400 parts of water and heated to 70° C., followed by stirring for 1 hour while maintaining the pH at 10.5 to 11.0 with sodium hydroxide. After cooling to the room temperature, by adjusting the pH at 7.0 to 8.0 with 35% hydrochloric acid, salting out by the addition of sodium chloride, and filtering, a wet cake containing a compound of Formula (20) was obtained.

the above reaction, which was then heated at 90° C., and stirred for 1 hour. After cooling to a room temperature, the pH was adjusted at 4.0 to 5.0 by the addition of sodium hydroxide, and then salting-out was conducted by addition of sodium chloride, followed by filtering to obtain a wet cake containing a compound of Formula (22).

[Formula 20]

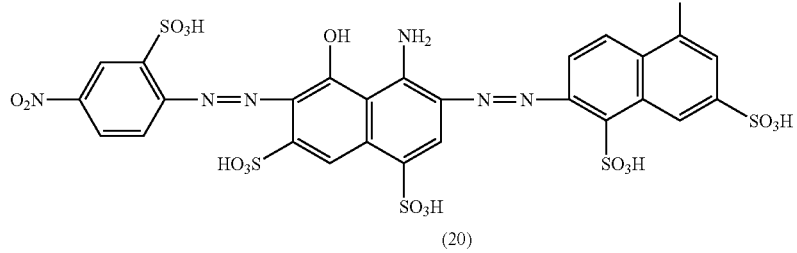

(20)

(3) In 100 parts of water 11.5 parts of 2-amino-5-acetylaminobenzenesulfonic acid was dissolved at pH 4.0 to 6.0 by the addition of sodium hydroxide and diazotized by the addition of 15.8 parts of 35% hydrochloric acid and 9.0 parts of 40% aqueous solution of sodium nitrite at 0 to 5° C. thereto. The diazo suspension was added dropwise into a solution where 14.2 parts of 3-carboxy-1-(4'-sulfophenyl)-5-pyrazolone is dissolved in 100 parts of water at pH 8.0 to 9.0 by the addition of sodium hydroxide, while maintaining the pH value of the solution at 8.0 to 9.0 with sodium carbonate at 10 to 20° C. After completion of the dropwise addition, a solution containing a compound of Formula (21) was obtained by stirring at pH 8.0 to 9.0 for 2 hours at 15 to 30° C.

[Formula 21]

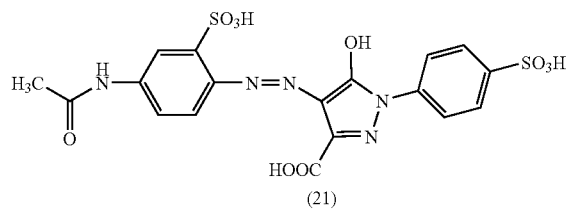

(21)

27.0 parts of 35% hydrochloric acid was added to the solution containing a compound of Formula (21) obtained by

[Formula 22]

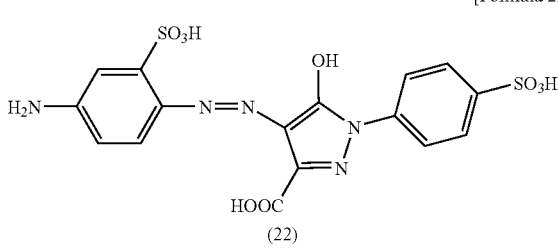

(22)

(4) The above obtained wet cake containing a compound of formula (22) was dissolved in 300 parts of water, while adjusting the pH at 6.0 to 8.0 with lithium hydroxide. To the solution obtained, 19.8 parts of 35% hydrochloric acid and 9.2 parts of 40% aqueous solution of sodium nitrite was added at 10 to 20° C. for diazotization. This diazo suspension was added dropwise to a solution where a wet cake containing a compound of Formula (20) was dissolved in 400 parts of water, while maintaining the pH value of the solution at 8.0 to 9.0 with lithium hydroxide, at 10 to 25° C. After completion of the dropwise addition, stirring for 2 hours at 15 to 30° C. at the pH 8.0 to 9.0, salting out by the addition of lithium chloride, and filtering were conducted. The obtained wet cake was dissolved in 400 parts of water, which was then crystallized by the addition of 1000 parts of ethanol and filtered. Furthermore, the obtained wet cake was dissolved in 200 parts of water, which was then crystallized by the addition of 1000 parts of ethanol, filtered, and dried to obtain 46.0 parts of an azo compound of Formula (23) (a compound No. 1 in Table 2) of the present invention. The maximum absorption wavelength (λ max) of this compound in water was 602 nm, and solubility in water (ammonia alkali) by filter paper spot was no less than 100 g/l.

[Formula 23]

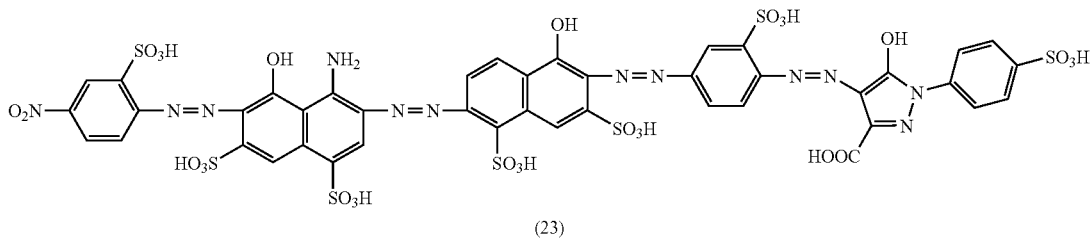

(23)

Example 2

In the same way as in (3) of Example 1 except that 11.5 parts of 2-amino-4-acetylaminobenzenesulfonic acid was used instead of 11.5 parts of 2-amino-5-acetylaminobenzenesulfonic acid in the process of (3) in Example 1, a wet cake containing a monoazo compound of Formula (24) was obtained.

[Formula 24]

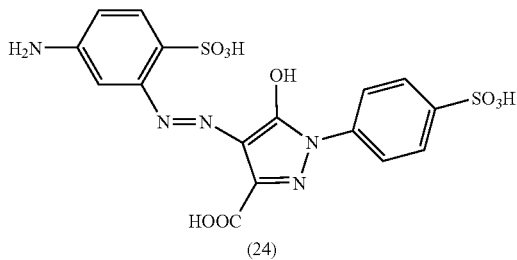

(24)

The above obtained wet cake containing a compound of formula (24) was dissolved in 300 parts of water, while adjusting the pH at 6.0 to 8.0 with sodium hydroxide. To the solution obtained, 19.8 parts of 35% hydrochloric acid and 9.2 parts of 40% aqueous solution of sodium nitrite was added at 10 to 20° C. for diazotization. This diazo suspension was added dropwise to a solution where a wet cake containing a compound of Formula (20) which was obtained in the same method as in the processes of (1) and (2) in Example 1 was dissolved in 400 parts of water, while maintaining the pH value of the solution at 8.0 to 9.0 with sodium carbonate, at 10 to 25° C. After completion of the dropwise addition, stirring for 2 hours at 15 to 30° C. at pH 8.0 to 9.0, salting out by the addition of sodium chloride, and filtering were conducted. The obtained wet cake was dissolved in 400 parts of water, which was then crystallized by the addition of 1000 parts of ethanol and filtered. Furthermore, the obtained wet cake was dissolved in 200 parts of water, which was then crystallized by the addition of 1000 parts of ethanol, filtered, and dried to obtain 52.0 parts of an azo compound of Formula (25) (a compound No. 13 in Table 3) of the present invention. The maximum absorption wavelength of this compound in water was 590 nm, and solubility in water (ammonia alkali) by filter paper spot was no less than 100 g/l.

[Formula 25]

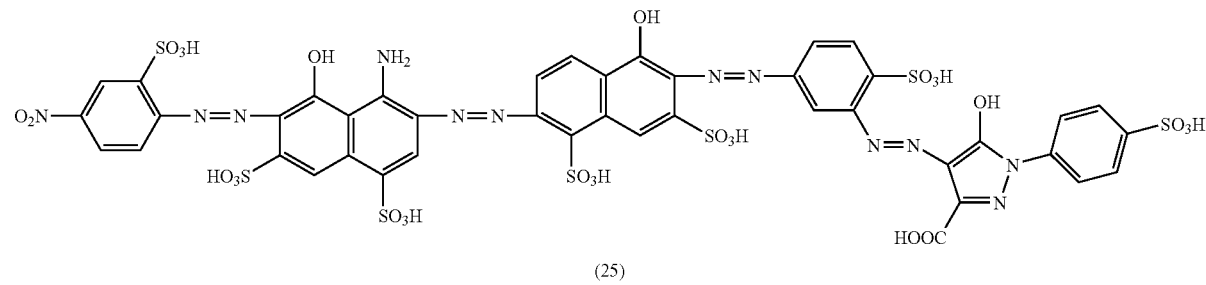

(25)

Example 3

In the same way as in Example 1 except that 15.5 parts of 2-amino-5-acetylaminobenzene-1,4-sulfonic acid was used instead of 11.5 parts of 2-amino-5-acetylaminobenzene-sulfonic acid in the process of (3) in Example 1, 54.0 parts of an azo compound of Formula (26) (a compound No. 9 in Table 3) was obtained. In this connection, 2-amino-5-acetylaminobenzene-1,4-disulfonic acid can be obtained easily by reaction of 2,5-diaminobenzene-1,4-disulfonic acid with acetic anhydride. The maximum absorption wavelength of this compound in water was 597 nm, and solubility in water (ammonia alkali) by filter paper spot was no less than 100 g/l.

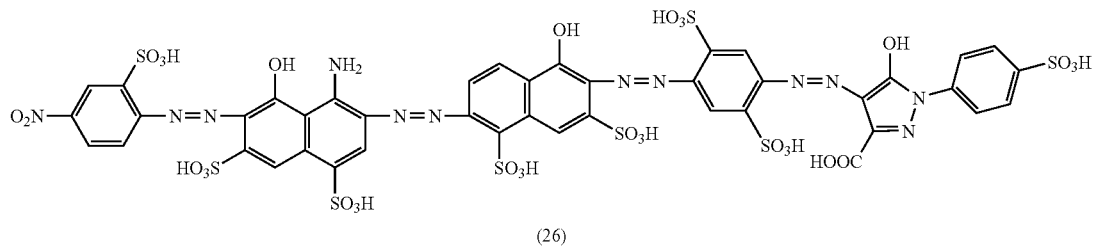

[Formula 26]

(26)

Example 4

In the same way as in Example 1 except that 18.2 parts of 3-carboxy-1-(2',5'-disulfophenyl)-5-pyrazolone was used instead of 14.2 parts of 3-carboxy-1-(4'-sulfophenyl)-5-pyrazolone in the process of (3) in Example 1, an azo compound of Formula (27) (a compound No. 21 in Table 5) was obtained. The maximum absorption wavelength of this compound in water was 600 nm, and solubility in water (ammonia alkali) by filter paper spot was no less than 100 g/l.

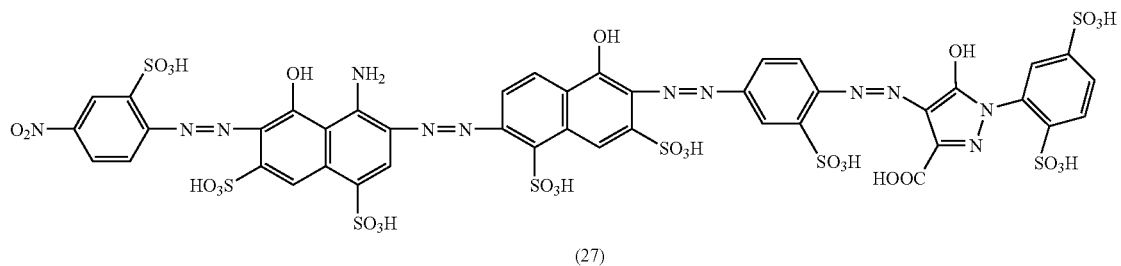

[Formula 27]

(27)

Example 5

In the same way as in Example 1 except that 14.4 parts of sodium 2-nitroaniline-4-sulfonate was used instead of 14.4 parts of sodium 4-nitroaniline-2-sulfonate in the process of (2) in Example 1, an azo compound of Formula (28) (a compound No. 22 in Table 5) was obtained. The maximum absorption wavelength of this compound in water was 602 nm, and solubility in water (ammonia alkali) by filter paper spot was no less than 100 g/l.

[Formula 28]

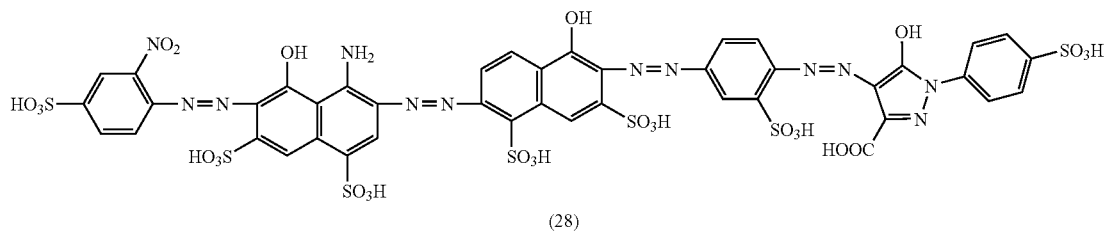

(28)

Example 6

In the same way as in Example 1 except that 14.4 parts of sodium 2-nitroaniline-4-sulfonate was used instead of 14.4 parts of sodium 4-nitroaniline-2-sulfonate in the process of (2) in Example 1, and 15.5 parts of 2-amino-5-acetylaminobenzene-1,4-disulfonic acid was used instead of 11.5 parts of 2-amino-5-acetylaminobenzenesulfonic acid in the process of (3), an azo compound of Formula (29) (a compound No. 23 in Table 5) was obtained. The maximum absorption wavelength of this compound in water was 599 nm, and solubility in water (ammonia alkali) by filter paper spot was no less than 100 g/l.

[Formula 29]

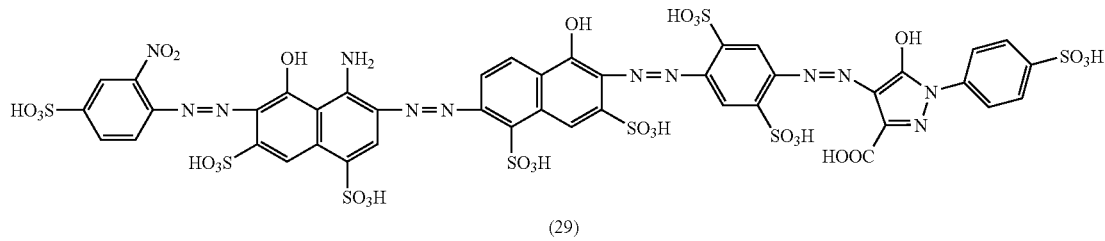

(29)

Example 7

In the same way as in Example 1 except that 16.2 parts of sodium 6-methoxy-4-nitroaniline-3-sulfonate was used instead of 14.4 parts of sodium 4-nitroaniline-2-sulfonate in the process of (2) in Example 1, an azo compound of Formula (30) (a compound No. 24 in Table 5) was obtained. The maximum absorption wavelength of this compound in water was 610 nm, and solubility in water (ammonia alkali) by filter paper spot was no less than 100 g/l.

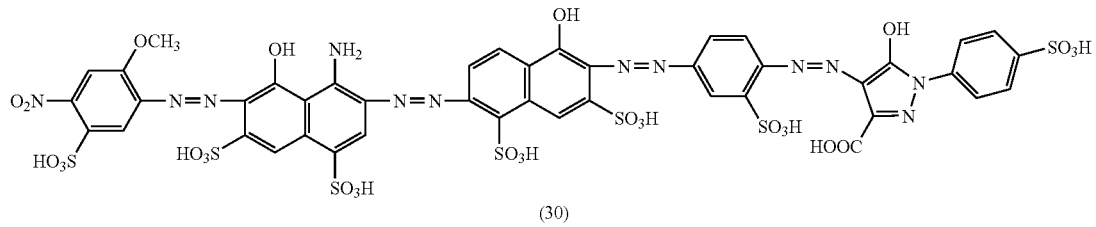

(30)

Example 8

(1) 24.0 parts of sodium 4-nitroaniline-2-sulfonate and 36.5 parts of 35% hydrochloric acid was added to 300 parts of water, heated to 60° C. and dissolved, followed by adding dropwise 24.9 parts of 30% hydrogen peroxide over 1 hour. After that, the solution was stirred for 6 hours at the same temperature, followed by eliminating insoluble matter by filtration, and the filtrate was cooled to 30° C., and subjected to salting out by the addition of sodium chloride. The precipitate was isolated by filtration to obtain a wet cake containing a compound of Formula (31).

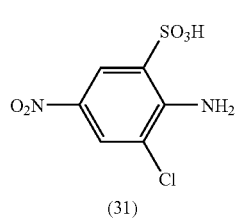

(31)

(2) The above obtained wet cake containing a compound of Formula (31) was dispersed in 180 parts of water and the pH value of the dispersion was adjusted at 7.0 to 8.0 by the addition of sodium hydroxide. 0.2 parts of ferric chloride and 2.2 parts of activated carbon were added thereto, followed by heating to 85° C., and 13.4 parts of 80% hydrazine hydrate was added dropwise over 30 minutes. After dropwise addition, the solution was stirred for 3 hours at the same temperature, followed by cooling to 30° C., and insoluble matter was eliminated by filtration. 20 parts of 35% hydrochloric acid was added to the filtrate, and the precipitate was isolated by filtration to obtain a wet cake containing a compound of Formula (32).

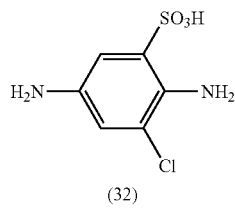

(32)

(3) The above obtained wet cake containing a compound of Formula (32) was dispersed in 180 parts of water and the pH value of the dispersion was adjusted at 7.0 to 8.0 by the addition of sodium hydroxide. 5.9 parts of acetic anhydride was added dropwise hereto at 20 to 30° C. over 5 minutes, which was then stirred at the same temperature for 1 hour. After cooling to 0 to 5° C., 15.0 parts of 35% hydrochloric acid and 9.5 parts of 40% aqueous solution of sodium nitrite were added for diazotization. This diazotized suspension was added dropwise to a solution where 14.7 parts of 3-carboxy-1-(4'-sulfophenyl)-5-pyrazolone was dissolved in 80 parts of water at pH 8.0 to 9.0 by the addition of sodium hydroxide, while maintaining the pH value of the solution at 8.0 to 9.0 with sodium carbonate at 10 to 20° C. After completion of dropwise addition, a solution containing a compound of Formula (33) was obtained by stirring at pH 8.0 to 9.0, for 2 hours at 15 to 30° C.

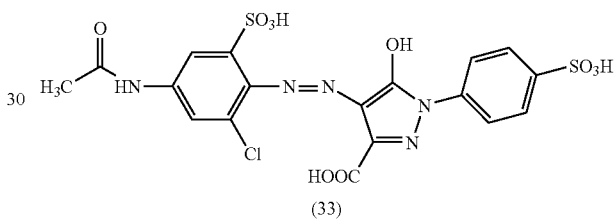

(33)

(4) 25.0 parts of 35% hydrochloric acid was added to the solution containing a compound of Formula (33) obtained in the above reaction, and then the solution was heated to 90° C. and stirred for 2 hours. After cooling to the room temperature, a wet cake containing a compound of Formula (34) was obtained by filtration.

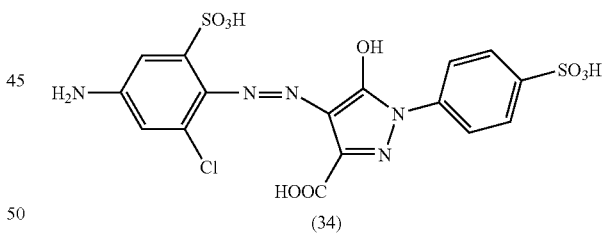

(34)

(5) The above obtained wet cake containing a compound of Formula (34) was dissolved in 300 parts of water while adjusting the pH at 6.0 to 8.0 with lithium hydroxide, and 9.2 parts of 40% aqueous solution of sodium nitrite was added thereto. This solution was added dropwise at 10 to 20° C. to a solution where 19.8 parts of 35% hydrochloric acid wasadded to 100 parts of water, for diazotization. This diazo suspension was added dropwise to a solution where a wet cake containing a compound of Formula (20) was dissolved in 400 parts of water, while maintaining the pH value of the solution at 8.0 to 9.0 with lithium hydroxide at 20 to 30° C. After completion of dropwise addition, the solution was stirred at pH 8.0 to 9.0 for 2 hours at 20 to 30° C., subjected to salting out by the addition of lithium chloride, and the precipitate was isolated by filtration. The obtained wet cake was dissolved in 600 parts of water and 1200 parts of 2-propanol was added thereto to crystallize. The precipitate was isolated by filtration. The obtained wet cake was dissolved in 550 parts of water, 1200 parts of 2-propanol was added thereto to crystallize, and the precipitate was isolated by filtration, and dried to obtain 48.0 parts of an azo compound of Formula (35) (a compound No. 25 in Table 5) of the present invention. The maximum absorption wavelength (λ max) of this compound in water was 591 nm, and solubility in water (ammonia alkali) by filter paper spot was no less than 100 g/l.

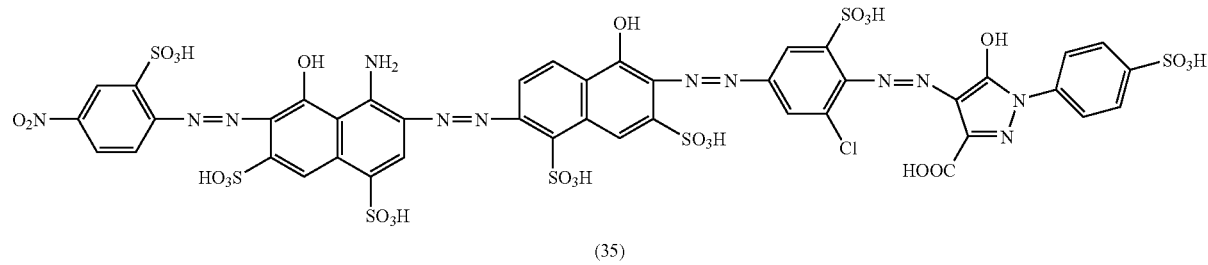

[Formula 35]

(35)

Example 9

(1) 18.1 parts of 5-nitroanthranilic acid and 32.0 parts of sulfamic acid were added to 60.0 parts of N-methylpyrolidone, and the solution was stirred for 8 hours at 130° C. This solution was cooled to 30° C., and then added dropwise to 400 parts of water. After stirring for 1 hour, insoluble matter was eliminated by filtration, and the pH value of the solution was adjusted at 0.5 or lower by the addition of 35% hydrochloric acid. Thereafter salting out with sodium chloride and isolation by filtration were conducted. The obtained wet cake was suspended in 300 parts of water, and the solution was adjusted to pH 3.5 to 4.0 by the addition of sodium hydroxide, followed by stirring for 1 hour at 60° C. After cooling to 30° C., insoluble matter was eliminated by filtration to obtain a solution containing a compound of Formula (36) below.

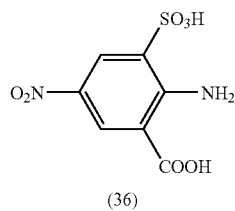

[Formula 36]

(36)

(2) The above obtained solution containing a compound of Formula (36) was cooled to 0 to 5° C., and 17.5 parts of 35% hydrochloric acid and 10.8 parts of 40% aqueous solution of sodium nitrite were added for diazotization. This diazo suspension was added dropwise to a solution where 16.7 parts of 3-carboxy-1-(4'-sulfophenyl)-5-pyrazolone was dissolved in 80 parts of water at pH 8.0 to 9.0 by the addition of sodium hydroxide, while maintaining the pH value of the solution at 8.0 to 9.0 with sodium carbonate at 10 to 20° C. After completion of dropwise addition, a solution containing a compound of Formula (37) was obtained by stirring at pH 8.0 to 9.0, at 15 to 30° C. for 2 hours.

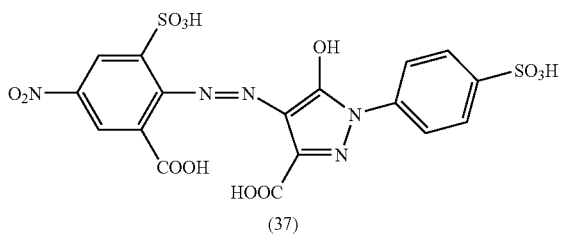

[Formula 37]

(37)

(3) A solution where 22.6 parts of sodium sulfide 9 hydrate was dissolved in 70 parts of water was added dropwise to the above obtained solution containing compound of Formula (37), at 15 to 30° C. After completion of dropwise addition, the solution was stirred for 2 hours at 15 to 30° C., and the pH was adjusted to acidic by the addition of 35% hydrochloric acid, and then insoluble matter was eliminated by filtration. A wet cake containing a compound of Formula (38) was obtained by salting out by the addition of sodium chloride and separating by filtration.

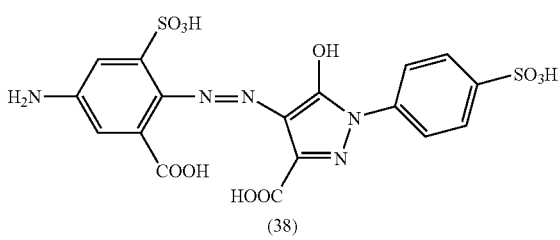

[Formula 38]

(38)

(4) In the same way as in Example 8 except that a wet cake containing a compound of Formula (38) obtained in the above reaction was used instead of a wet cake containing a compound of Formula (34) in the process of (5) in Example 8, an azo compound of Formula (39) (a compound No. 26 in Table 5) was obtained. The maximum absorption wavelength of this compound in water was 592 nm, and solubility in water (ammonia alkali) by filter paper spot was no less than 100 g/l.

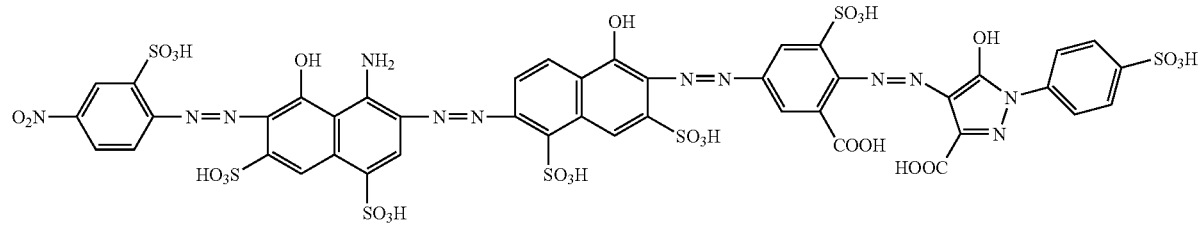

(39)

Example 10

In the same way as in Example 1 except that 14.8 parts of 3-carboxy-1-(3',5'-dicarboxyphenyl)-5-pyrazolone was used instead of 14.2 parts of 3-carboxy-1-(4'-sulfophenyl)-5-pyrazolone in the process of (3) in Example 1, an azo compound of Formula (40) (a compound No. 27 in Table 5) was obtained. The maximum absorption wavelength of this compound in water was 603 nm, and solubility in water (ammonia alkali) by filter paper spot was no less than 100 g/l.

In Table 6, "a compound obtained in the above Examples" means respectively the compound of Formula (23) obtained in Example 1 for Example 11, the compound of Formula (25) obtained in Example 2 for Example 12, the compound of Formula (26) obtained in Example 3 for Example 13, the compound of Formula (27) obtained in Example 4 for Example 14, the compound of Formula (28) obtained in Example 5 for Example 15, the compound of Formula (29) obtained in Example 6 for Example 16, the compound of Formula (30) obtained in Example 7 for Example 17, the

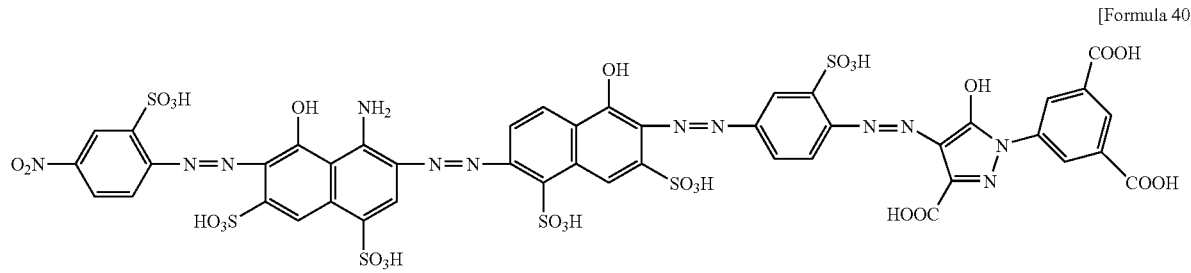

(40)

Examples 11 to 20

(A) Preparation of an Ink

An ink composition was prepared by mixing the components described below, followed by filtering with a 0.45 μm membrane filter to obtain an ink composition according to the present invention for ink-jet. Ion exchange water was used as water. Water and ammonium hydroxide were added in order that the ink composition had pH=8 to 9.

TABLE 6

| | |
|---|---|
| Compound obtained in the above Example (using the one subjected to desalting treatment) | 5.0 part |
| Glycerine | 5.0 part |
| Urea | 5.0 part |
| N-methyl-2-pyrolidone | 4.0 part |
| Isopropyl alcohol | 3.0 part |
| Butylcarbitol | 2.0 part |
| Surfactant (Surfynol 105 from Nissin Chemical Industry Co., Ltd.) | 0.1 part |
| Water + ammonium hydroxide | 75.9 part |
| Total | 100.0 part | compound of Formula (35) obtained in Example 8 for Example 18, the compound of Formula (39) obtained in Example 9 for Example 19, the compound of Formula (40) obtained in Example 10 for Example 20. This water-based ink composition did not cause precipitation separation during storage thereof, and did not generate changed physical property after storage for a long period of time.

(B) Ink-jet Printing

Using each ink composition obtained above, by an ink-jet printer (Trade name BJ-S630 from Canon Inc.), ink-jet recording was conducted on three types of paper of a Plain Paper (LBP PAPER LS-500 from Canon Inc.), Professional Glossy Paper PR (Professional Photopaper PR-101 from Canon Inc.), and Professional Glossy Paper PM (a paper for PM photograph (glossy), KA420PSK of Epson Co., Ltd.).

On printing, an image pattern was made so as to obtain gradations of several stages in reflection density, and a black colored print of half tone was obtained. As a gray scale mode is used on printing, each recording liquid of yellow, cyan, and magenta is not used together besides a black colored recording liquid. Among testing methods described below, in evaluation of printing density which is an item to be evaluated using a calorimeter, on measuring reflection density, D value, of a print, the highest portion of this D value was used.

Further, on measuring of light fastness and ozone gas fastness which are similarly items to be evaluated using a calorimeter, measurement was conducted using a portion of gradations wherein reflection density, D value, of a print before testing is closest to 1.0.

(C) Evaluation of a Recorded Image

Concerning a recorded image according to a water-based ink composition according to the present invention, evaluation was conducted on 3 items, that is, printing density, change in hue after light fastness testing, and change in hue after ozone gas fastness testing. In this connection, the ozone gas fastness test and the light fastness test were conducted using only Professional Glossy Papers PR and PM. The results are shown in Table 7-1 and 7-2. The testing methods are shown below.

1) Evaluations of Printing Density

Hue density of a recorded image was measured using GRETAG SPM50 (from GRETAG Co., Ltd.), and printing density D value was calculated. Judgment criteria are shown below.

○: a Plain Paper: 1.2≦D, a Glossy Paper: 2.0≦D
Δ: a Plain Paper: 1.0≦D<1.2, a Glossy Paper: 1.8≦D<2.0
x: a Plain Paper: D<1.0, a Glossy Paper: D<1.8

2) Light Fastness Test

Using a xenon weatherometer Ci4000 (from ATLAS Co., Ltd.), a printing sample was irradiated for 50 hours at illuminance of 0.36 W/m². After the test, using the above described colorimetric system, residual percentage of hue density before and after the test was measured. Judgment was conducted by the guideposts as shown below.

○: residual percentage: no less than 95%
Δ: residual percentage: less than 95% and no less than 90%
x: residual percentage: less than 90%

3) Ozone Gas Fastness Test

Using an ozone weatherometer (from Suga Testing Machine Co., Ltd.), a printing sample was left for 6 hours under ozone concentration of 40 ppm, humidity of 60% RH and temperature of 24° C. After the test, using the above described calorimetric system, residual percentage of density before and after the test was measured. Judgment was conducted by the guideposts as shown below.

○: ΔE is less than 15 when testing for 6 hours,
Δ: ΔE is no less than 15 and less than 30 when testing for 6 hours
x: ΔE is no less than 30 when testing for 6 hours Comparative Example 1

Using, for comparison, a coloring matter (the following Formula (41)) of 1 in Table 1-1 described in Patent Literature 1 as a coloring matter for water-soluble ink-jet, an ink composition was prepared by the same ink-composition as in Example 11 to 20. The obtained evaluation results of printing density, light fastness, and ozone gas fastness of a recorded image are shown in Table 7-2.

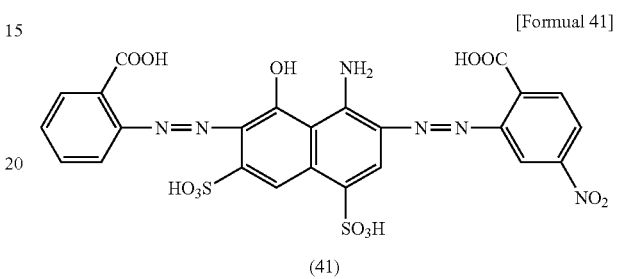

(41)

Comparative Example 2

Using a coloring matter AN-250 (the following Formula (42)) described in Example 1 of Patent Literature 3 as a coloring matter for water-soluble ink-jet, an ink composition was prepared by the same ink-composition as in Example 11 to 20. The obtained evaluation results of printing density, light fastness, and ozone gas fastness of a recorded image are shown in Table 7-2.

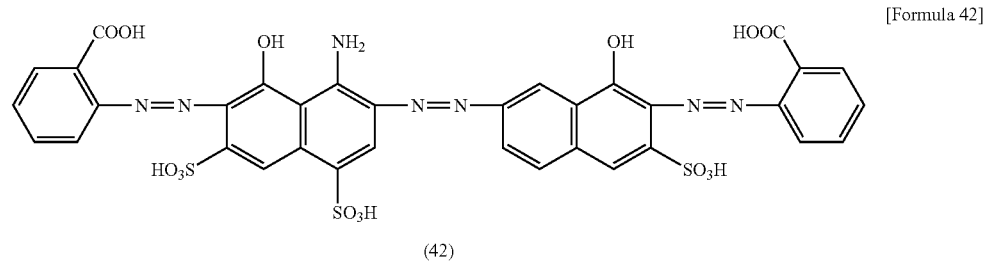

(42)

TABLE 7-1

|  | Printing density | Light fastness | Ozone gas fastness |
|---|---|---|---|
| Example 11 (Formula (23)) | | | |
| Plain Paper | ○ | ○ | — |
| Professional Glossy Paper PR | ○ | ○ | Δ |
| Professional Glossy Paper PM | ○ | ○ | ○ |
| Example 12 (Formula (25)) | | | |
| Plain Paper | ○ | ○ | — |
| Professional Glossy Paper PR | ○ | ○ | Δ |
| Professional Glossy Paper PM | ○ | ○ | ○ |

TABLE 7-1-continued

| | Printing density | Light fastness | Ozone gas fastness |
|---|---|---|---|
| Example 13 (Formula (26)) | | | |
| Plain Paper | ○ | ○ | — |
| Professional Glossy Paper PR | ○ | ○ | Δ |
| Professional Glossy Paper PM | ○ | ○ | ○ |
| Example 14 (Formula (27)) | | | |
| Plain Paper | ○ | ○ | — |
| Professional Glossy Paper PR | ○ | ○ | Δ |
| Professional Glossy Paper PM | ○ | ○ | ○ |
| Example 15 (Formula (28)) | | | |
| Plain Paper | ○ | ○ | — |
| Professional Glossy Paper PR | ○ | ○ | Δ |
| Professional Glossy Paper PM | Δ | ○ | ○ |
| Example 16 (Formula (29)) | | | |
| Plain Paper | ○ | ○ | — |
| Professional Glossy Paper PR | ○ | ○ | Δ |
| Professional Glossy Paper PM | ○ | ○ | ○ |

TABLE 7-2

| | Printing density | Light fastness | Ozone gas fastness |
|---|---|---|---|
| Example 17 (Formula (30)) | | | |
| Plain Paper | ○ | ○ | — |
| Professional Glossy Paper PR | ○ | ○ | Δ |
| Professional Glossy Paper PM | ○ | ○ | ○ |
| Example 18 (Formula (35)) | | | |
| Plain Paper | ○ | ○ | — |
| Professional Glossy Paper PR | ○ | ○ | Δ |
| Professional Glossy Paper PM | ○ | ○ | ○ |
| Example 19 (Formula (39)) | | | |
| Plain Paper | ○ | ○ | — |
| Professional Glossy Paper PR | ○ | ○ | Δ |
| Professional Glossy Paper PM | ○ | ○ | Δ |
| Example 20 (Formula (40)) | | | |
| Plain Paper | ○ | ○ | — |
| Professional Glossy Paper PR | ○ | ○ | ○ |
| Professional Glossy Paper PM | ○ | ○ | ○ |
| Comparative Example 1 (Formula (41)) | | | |
| Plain Paper | ○ | Δ | — |
| Professional Glossy Paper PR | ○ | Δ | X |
| Professional Glossy Paper PM | ○ | ○ | Δ |
| Comparative Example 2 (Formula (42)) | | | |
| Plain Paper | ○ | Δ | — |
| Professional Glossy Paper PR | ○ | Δ | X |
| Professional Glossy Paper PM | ○ | ○ | X |

Judging from Table 7-1 and Table 7-2, it is found that an ink composition comprising an azo compound of the present invention has high printing density, and is excellent in light fastness and ozone gas fastness as compared with a conventional black colored dye (Comparative Examples). In addition, an azo compound of the present invention having high solubility can make it possible to design a stably high-concentration ink composition.

INDUSTRIAL APPLICABILITY

An ink composition comprising an azo compound of the present invention is used suitably as a black ink liquid for ink-jet recording and writing tools.

The invention claimed is:

1. An azo compound represented by Formula (1) as shown below or a salt thereof:

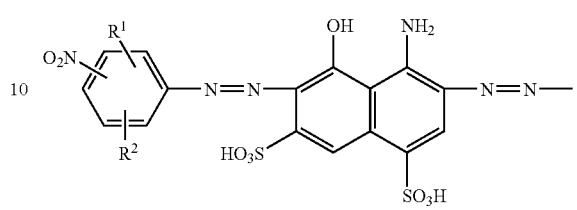

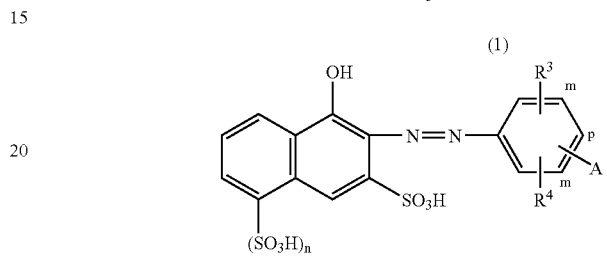

wherein, A represents the following Formula (2): A's substitution position is the meta-position or the para-position to an azo group: each of $R^1$ and $R^2$ independently represents a hydrogen atom; a halogen atom; a cyano group; a carboxyl group; a sulfo group; a sulfamoyl group; an N-alkylaminosulfonyl group; an N-phenylaminosulfonyl group; a phospho group; a nitro group; an acyl group; a ureide group; a (C1 to C4) alkyl group which may be substituted with a hydroxyl group or a (C1 to C4) alkoxy group; a (C1 to C4) alkoxy group which may be substituted with a hydroxyl group, a (C1 to C4) alkoxy group, a sulfo group or a carboxyl group; or an acylamino group which can be substituted with a (C1 to C4) alkoxy group, a sulfo group or a carboxyl group: each of $R^3$ and $R^4$ independently represents a hydrogen atom; a halogen atom; a cyano group; a carboxyl group; a sulfo group; a nitro group; a (C1 to C4) alkyl group; a hydroxyl group; or a (C1 to C4) alkoxy group which may be substituted with a (C1 to C4) alkoxy group or a sulfo group: and n represents 0 or 1:

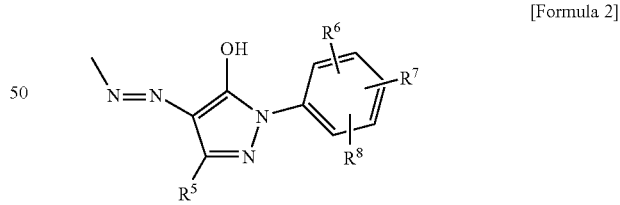

wherein, $R^5$ represents a cyano group; a carboxyl group; a (C1 to C4) alkyl group; a (C1 to C4) alkoxycarbonyl group; or a phenyl group: and each of $R^6$, $R^7$ and $R^8$ independently represents a hydrogen atom; a halogen atom; a cyano group; a carboxyl group; a sulfo group; a nitro group; a (C1 to C4) alkyl group; a (C1 to C4) alkoxy group which may be substituted with a hydroxyl group, a (C1 to 4) alkoxy group or a sulfo group; or an acylamino group which may be substituted with a hydroxyl group, a (C1 to C4) alkoxy group or a sulfo group.

2. The azo compound or the salt thereof according to claim 1, wherein in Formula (1), $R^1$ is a carboxyl group, a sulfo group or a (C1 to C4) alkoxy group, and $R^2$ is a hydrogen atom or a sulfo group.

3. The azo compound or the salt thereof according to claim 2, wherein in Formula (1), for positions of $NO_2$, $R^1$ and $R^2$,

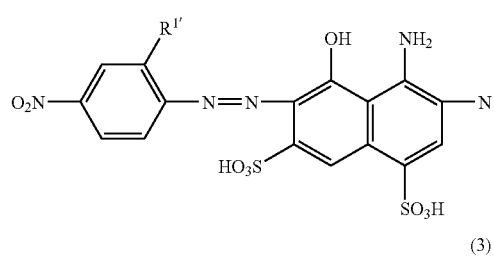

(3)

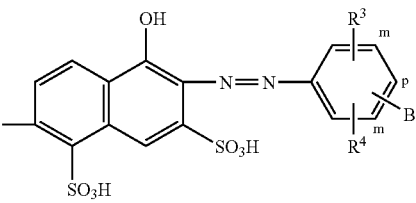

[Formula 3]

$NO_2$ is at the para-position, $R^1$ is at the ortho-position and $R^2$ is at the meta-position, or when $NO_2$ is at the ortho-position, $R^1$ is a sulfo group at the para-position and $R^2$ is a hydrogen atom.

4. The azo compound or the salt thereof according to claim 1, wherein in Formula (1), n is 1, $R^3$ is a sulfo group or a carboxyl group, and $R^4$ is a hydrogen atom, a (C1 to C4) alkyl group, a $NO_2$ group, a sulfo group, a (C1 to C4) alkoxy group, a halogen atom or a carboxyl group.

5. The azo compound or the salt thereof according to claim 1, wherein in Formula (1), n is 1, $R^3$ is a sulfo group, and $R^4$ is a hydrogen atom, a sulfo group, a chlorine atom, or a carboxyl group.

6. The azo compound or the salt thereof according to claim 1, wherein in Formula (2), $R^5$ is a carboxyl group, $R^6$ is a hydrogen atom, a halogen atom or a (C1 to C4) alkyl group, $R^7$ is a carboxyl group or a sulfo group, and $R^8$ is a hydrogen atom, a halogen atom, a carboxyl group or a sulfo group.

7. The azo compound or the salt thereof according to claim 1, wherein in Formula (2), $R^5$ is a carboxyl group, and a phenyl group substituted with $R^6$, $R^7$ and $R^8$ is a p-sulfophenyl group, a 2,5-disulfophenyl group or a 3,5-dicarboxyphenyl group.

8. The azo compound or the salt thereof according to, wherein in Formula (1) $R^2$ is a hydrogen atom and $R^1$ is a carboxyl group or a sulfo group.

9. The azo compound or the salt thereof according to claim 1, wherein in Formula (1), $R^1$ is a carboxyl group, a sulfo group or a (C1 to C4) alkoxy group: $R^2$ is a hydrogen atom or a sulfo group: for positions of $NO_2$, $R^1$ and $R^2$, $NO_2$ is at the para-position, $R^1$ is at the ortho-position and $R^2$ is at the meta-position, or when $NO_2$ is at the ortho-position, $R^1$ is a sulfo group at the para-position and $R^2$ is a hydrogen atom, n is 1, $R^3$ is a sulfo group, and $R^4$ is a hydrogen atom, a sulfo group, a chlorine atom or a carboxyl group, and in Formula (2), $R^5$ is a carboxyl group, and a phenyl group substituted with $R^6$, $R^7$ and $R^8$ is a p-sulfophenyl group, a 2,5-disulfophenyl group or a 3,5-dicarboxyphenyl group.

10. An azo compound or a salt thereof according to, wherein the azo compound is represented by Formula (3) as shown below:

wherein, B represents Formula (4): B's substitution position is the meta-position or the para-position to an azo group: $R^1$ represents a sulfo group or a carboxyl group: and $R^3$ and $R^4$ have the same meanings as in Formula (1) of claim 1:

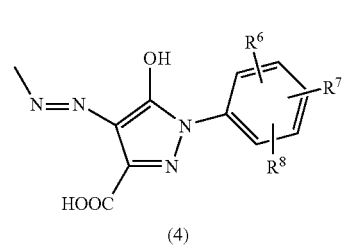

[Formula 4]

(4)

wherein, $R^6$, $R^7$ and $R^8$ have the same meanings as in Formula (2) in claim 1.

11. The azo compound or the salt thereof according to claim 10, wherein $R^3$ is a hydrogen atom, a halogen atom, a carboxyl group, a sulfo group, a nitro group or a (C1 to C4) alkyl group: $R^4$ is a hydrogen atom, a sulfo group or a nitro group: $R^6$ is a hydrogen atom, a halogen atom or a (C1 to C4) alkyl group: $R^7$ is a sulfo group or a carboxyl group: and $R^8$ is a hydrogen atom, a halogen atom, a carboxyl group or a sulfo group.

12. An azo compound or a salt thereof according to, wherein the azo compound is represented by Formula (5) as shown below:

[Formula 5]

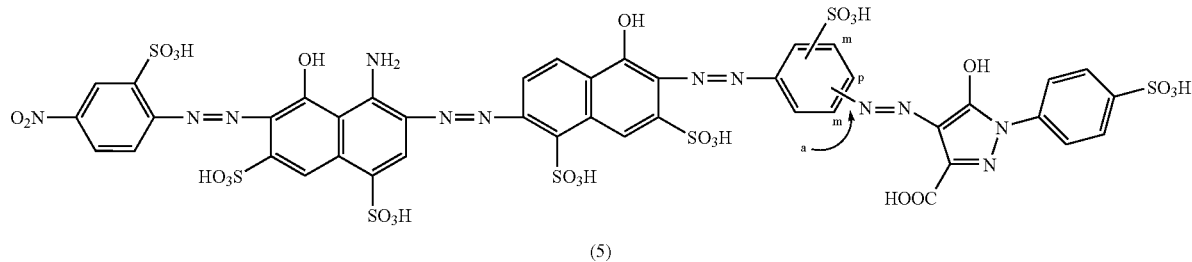

(5)

wherein, bond a's bonding position is the meta-position or the para-position to an azo group.

13. The salt of the azo compound according to, wherein the salt is a lithium salt, a sodium salt, a potassium salt, an ammonium salt, or an ammonium salt represented by the general Formula (6):

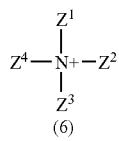

[Formula 6]

(6)

wherein, each of $Z^1$, $Z^2$, $Z^3$ and $Z^4$ independently represents a hydrogen atom, an alkyl group, a hydroxyalkyl group or a hydroxyalkoxyalkyl group.

14. An ink composition characterized by comprising at least one kind of an azo compound or a salt thereof according to claim 1.

15. A recording method of ink-jet printing by applying the ink composition according to claim 14 to a record-receiving material by an ink-jet printer.

16. The recording method of ink-jet printing according to claim 15, wherein a record-receiving material for a method of ink-jet printing is a sheet for transmitting information.

17. The recording method of ink-jet printing according to claim 16, characterized by that a sheet for transmitting information comprises a white inorganic matter.

18. An ink-jet printer loaded with an ink container filled with the ink composition according to claim 14.

19. A colored object colored by the azo compound or the salt thereof according to claim 1.

20. The azo compound or the salt thereof according to, wherein in Formula (1), A's substitution position is the meta-position or the para-position to an azo group: each of $R^1$ and $R^2$ is independently a hydrogen atom; a carboxyl group; a sulfo group; or a (C1 to C4) alkoxy group which may be substituted with a sulfo group: each of $R^3$ and $R^4$ is independently a hydrogen atom; a halogen atom; a carboxyl group; a sulfo group; a nitro group; a (C1 to C4) alkyl group; or a (C1 to C4) alkoxy group: and n is 0 or 1, and in Formula (2), $R^5$ is a cyano group; a carboxyl group; a (C1 to C4) alkyl group; or a phenyl group: and each of $R^6$, $R^7$ and $R^8$ is independently a hydrogen atom, a halogen atom; a carboxyl group; a sulfo group; or a (C1 to C4) alkyl group.

21. The compound according to claims 1, 10 or 20, wherein a substitution position of substitution A in Formula (1) or substitution B in Formula (3) is the para-position to an azo group.

22. The azo compound and the salt thereof according to claim 10, wherein $R^1$ is a sulfo group: B's substitution position is the para-position to an azo group: $R^3$ is a sulfo group substituted at the meta-position: $R^4$ is a halogen atom or a carboxyl group substituted at the meta-position which is deferent from $R^3$: $R^6$ and $R^8$ are hydrogen atoms: and $R^7$ is a sulfo group.

23. The azo compound or the salt thereof according to claim 11, wherein $R^7$ is a sulfo group.

24. An ink composition characterized by comprising at least one kind of an azo compound or a salt thereof according to any one of claims 20, 22 and 23.

25. A recording method of ink-jet printing by applying the ink composition according to claim 24 to a record-receiving material by an ink-jet printer.

* * * * *